(12) United States Patent
Limon

(10) Patent No.: US 10,702,149 B2
(45) Date of Patent: Jul. 7, 2020

(54) APPARATUS, SYSTEM AND METHOD OF DETERMINING A PUPILLARY DISTANCE

(71) Applicant: 6 OVER 6 VISION LTD., Kfar Saba (IL)

(72) Inventor: Ofer Limon, Kfar Saba (IL)

(73) Assignee: 6 OVER 6 VISION LTD., Kfar Saba (IL)

( * ) Notice: Subject to any disclaimer, the term of this patent is extended or adjusted under 35 U.S.C. 154(b) by 0 days.

(21) Appl. No.: 15/572,889

(22) PCT Filed: May 10, 2016

(86) PCT No.: PCT/IB2016/052671
§ 371 (c)(1),
(2) Date: Nov. 9, 2017

(87) PCT Pub. No.: WO2016/181308
PCT Pub. Date: Nov. 17, 2016

(65) Prior Publication Data
US 2018/0140186 A1    May 24, 2018

Related U.S. Application Data

(60) Provisional application No. 62/159,490, filed on May 11, 2015.

(51) Int. Cl.
*A61B 3/11* (2006.01)
*G06K 9/46* (2006.01)
*G02C 13/00* (2006.01)

(52) U.S. Cl.
CPC ............... *A61B 3/111* (2013.01); *G06K 9/46* (2013.01); *G02C 13/005* (2013.01)

(58) Field of Classification Search
CPC ........... A61B 3/10; A61B 3/00; A61B 3/0083; A61B 3/0033; A61B 3/0025; A61B 3/11;
(Continued)

(56) References Cited

U.S. PATENT DOCUMENTS 5,231,674 A * 7/1993 Cleveland ............. A61B 3/113
351/210
6,535,223 B1  3/2003 Foley
(Continued)

FOREIGN PATENT DOCUMENTS

CA    2692473     1/2009
EP    1728467     12/2006
(Continued)

OTHER PUBLICATIONS

International Preliminary Report on Patentability for PCT/IB2016/052671, dated Mar. 1, 2018, 7 pages.
(Continued)

*Primary Examiner* — Jie Lei
(74) *Attorney, Agent, or Firm* — Dorsey & Whitney LLP

(57) ABSTRACT

Some demonstrative embodiments include apparatuses, systems and/or methods of determining a pupillary distance. For example, a product may include one or more tangible computer-readable non-transitory storage media including computer-executable instructions operable to, when executed by at least one computer processor, enable the at least one computer processor to implement operations of measuring a pupillary distance between pupils of a user. The operations may include receiving a captured image comprising first and second reflections of a light of a light source, the first reflection comprising a reflection of the light from a first pupil of the user, and the second reflection comprising a reflection of the light from a second pupil of the user; and determining the pupillary distance based on locations of the first and second reflections in the captured image and an estimated distance between an image capturing device and pupils of the user, when the image is captured.

24 Claims, 13 Drawing Sheets

(58) Field of Classification Search
CPC ........... A61B 3/111; A61B 3/112; A61B 3/14; A61B 3/1208; A61B 3/103; G02C 13/005; G02C 13/003; G06K 9/46
USPC .................. 351/204, 206, 208, 218, 246
See application file for complete search history.

(56) References Cited

U.S. PATENT DOCUMENTS

| | | |
|---|---|---|
| 8,459,792 B2 | 6/2013 | Wilson et al. |
| 2005/0068495 A1 | 3/2005 | Jojiki |
| 2010/0220285 A1* | 9/2010 | Simmonds ........... G02C 13/005 351/204 |
| 2011/0267578 A1 | 11/2011 | Wilson |
| 2014/0253875 A1 | 9/2014 | Le Gallou et al. |

FOREIGN PATENT DOCUMENTS

| | | |
|---|---|---|
| EP | 2857939 | 4/2015 |
| RU | 2550011 | 5/2015 |

OTHER PUBLICATIONS

International Search Report and Written Opinion for PCT/IB2016/052671, dated Aug. 29, 2016, 10 pages.
Office Action for Israeli Patent Application No. 255571, dated Dec. 24, 2018, 3 pages.
Office Action for Chinese Patent Application No. 201680040604.6, dated Apr. 26, 2019, 13 pages (Including 5 pages of English translation).
European Search Report for European Patent Application No. 16792276.4, dated Jan. 7, 2019, 7 pages.
Office Action for Russian Patent Application No. 2017139578, dated Aug. 9, 2019, 20 pages (Including 10 pages of English translation).
Sokolov V.O. et al., Discussion of the problems of optometry. Axis of eyes. Interpupillary distance—Ophthalmic journal vol. 1 (3), 2008, 3 pages.
Office Action for Russian Patent Application No. 2017139578/14, dated Dec. 16, 2019, 20 pages (Including 10 pages of English translation).
Office Action for Chinese Patent Application No. 201680040604.6, dated Jan. 16, 2020, 8 pages (Including 3 pages of English translation).
Office Action for Australian Patent Application No. 2016261275, dated Feb. 7, 2020, 5 pages.

* cited by examiner

APPARATUS, SYSTEM AND METHOD OF DETERMINING A PUPILLARY DISTANCE

CROSS REFERENCE

This Application claims the benefit of and priority from U.S. Provisional Patent Application No. 62/159,490 entitled "APPARATUS, SYSTEM AND METHOD OF DETERMINING A PUPILLARY DISTANCE", filed May 11, 2015, the entire disclosure of which is incorporated herein by reference.

TECHNICAL FIELD

Embodiments described herein generally relate to determining a pupillary distance.

BACKGROUND

A pupillary distance (PD) between pupils of a user may be measured, e.g., in addition to the refractive prescription for eyeglasses, e.g., mono-focal or multi-focal eyeglasses.

Optical centers of eyeglasses may be configured to coincide with a line of sight of the user, for example, to provide clear and convenient vision.

Multi-Focal (MF) spectacles, which may have a narrow distant vision zone, may require higher accuracy in the PD measurement than mono-focal spectacles.

The PD may be stated as two unequal numbers of distances from a frame center, e.g., a center of a nose of the user, for example, if symmetry in the PD is not always a constitution, e.g., in strabismus cases.

Discrepancy in the pupillary distance may lead, for example, to double vision, headaches, and/or other unwanted effects.

A degree of a possible error in the pupillary distance may depend on the power of the lens, e.g., an Rx of spectacles. For example, for a low power of the lens, larger errors in the pupillary distance may not affect a vision of the user.

An error tolerance of the pupillary distance may not be symmetric. In one example, if a measured PD of a user is less than an actual PD of the user, e.g., a negative error, the user may be able to compensate for the negative error, for example, by a slight accommodation of the eyes, which may lead to eye convergence that may reduce the actual PD of the user. In another example, a measured PD of a user, which is larger than an actual PD of the user, e.g., a positive error, may result in some degree of double vision and/or other inconveniences.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION

Figure 1:
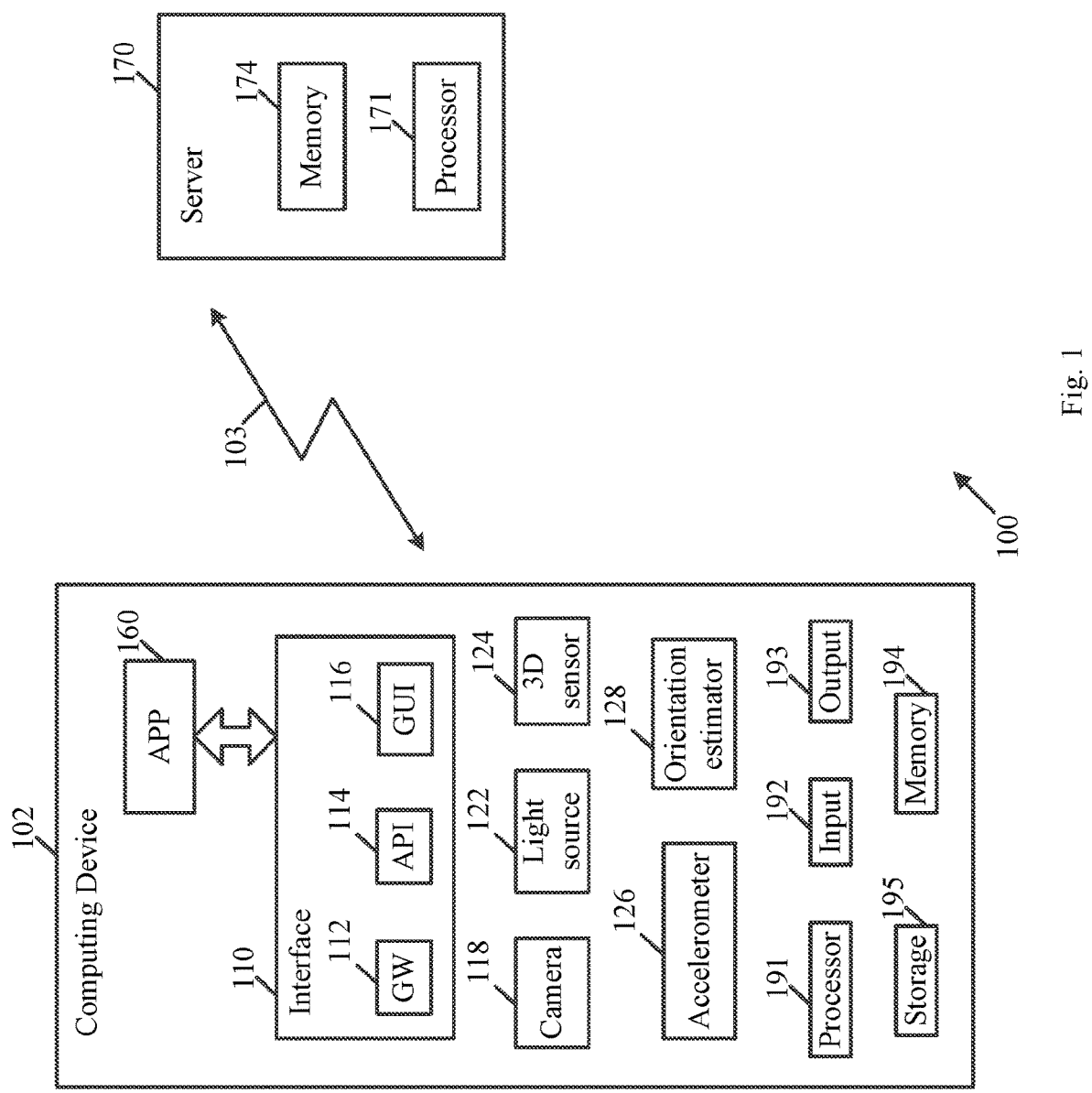
FIG. 1 is a schematic block diagram illustration of a system, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Some portions of the following detailed description are presented in terms of algorithms and symbolic representations of operations on data bits or binary digital signals within a computer memory. These algorithmic descriptions and representations may be the techniques used by those skilled in the data processing arts to convey the substance of their work to others skilled in the art.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Discussions herein utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments" etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first", "second", "third" etc., to describe a common object, merely indicate that different instances of like objects are being referred to, and are not intended to imply that the objects so described must be in a given sequence, either temporally, spatially, in ranking, or in any other manner.

Some embodiments, for example, may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some demonstrative embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a FLASH memory, a rigid magnetic disk, and an optical disk. Some demonstrative examples of optical disks include compact disk-read only memory (CD-ROM), compact disk-read/write (CD-R/W), and DVD.

In some demonstrative embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some demonstrative embodiments, input/output or I/O devices (including but not limited to keyboards, displays, pointing devices, etc.) may be coupled to the system either directly or through intervening I/O controllers. In some demonstrative embodiments, network adapters may be coupled to the system to enable the data processing system to become coupled to other data processing systems or remote printers or storage devices, for example, through intervening private or public networks. In some demonstrative embodiments, modems, cable modems and Ethernet cards are demonstrative examples of types of network adapters. Other suitable components may be used.

Some embodiments may include one or more wired or wireless links, may utilize one or more components of wireless communication, may utilize one or more methods or protocols of wireless communication, or the like. Some embodiments may utilize wired communication and/or wireless communication.

Some embodiments may be used in conjunction with various devices and systems, for example, a mobile phone, a Smartphone, a mobile computer, a laptop computer, a notebook computer, a tablet computer, a handheld computer, a handheld device, a Personal Digital Assistant (PDA) device, a handheld PDA device, a mobile or portable device, a non-mobile or non-portable device, a cellular telephone, a wireless telephone, a device having one or more internal antennas and/or external antennas, a wireless handheld device, or the like.

Reference is now made to FIG. 1, which schematically illustrates a block diagram of a system 100, in accordance with some demonstrative embodiments.

As shown in FIG. 1, in some demonstrative embodiments system 100 may include a device 102.

In some demonstrative embodiments, device 102 may be implemented using suitable hardware components and/or software components, for example, processors, controllers, memory units, storage units, input units, output units, communication units, operating systems, applications, or the like.

In some demonstrative embodiments, device 102 may include, for example, a computing device, a mobile phone, a Smartphone, a Cellular phone, a notebook, a mobile computer, a laptop computer, a notebook computer, a tablet computer, a handheld computer, a handheld device, a PDA device, a handheld PDA device, a wireless communication device, a PDA device which incorporates a wireless communication device, or the like.

In some demonstrative embodiments, device 102 may include, for example, one or more of a processor 191, an input unit 192, an output unit 193, a memory unit 194, and/or a storage unit 195. Device 102 may optionally include other suitable hardware components and/or software components. In some demonstrative embodiments, some or all of the components of one or more of device 102 may be enclosed in a common housing or packaging, and may be interconnected or operably associated using one or more wired or wireless links In other embodiments, components of one or more of device 102 may be distributed among multiple or separate devices.

In some demonstrative embodiments, processor 191 may include, for example, a Central Processing Unit (CPU), a Digital Signal Processor (DSP), one or more processor cores, a single-core processor, a dual-core processor, a multiple-core processor, a microprocessor, a host processor, a controller, a plurality of processors or controllers, a chip, a microchip, one or more circuits, circuitry, a logic unit, an Integrated Circuit (IC), an Application-Specific IC (ASIC), or any other suitable multi-purpose or specific processor or controller. Processor 191 may execute instructions, for example, of an Operating System (OS) of device 102 and/or of one or more suitable applications.

In some demonstrative embodiments, input unit 192 may include, for example, a keyboard, a keypad, a mouse, a touch-screen, a touch-pad, a track-ball, a stylus, a microphone, or other suitable pointing device or input device. Output unit 193 may include, for example, a monitor, a screen, a touch-screen, a flat panel display, a Light Emitting Diode (LED) display unit, a Liquid Crystal Display (LCD) display unit, a plasma display unit, one or more audio speakers or earphones, or other suitable output devices.

In some demonstrative embodiments, memory unit 194 includes, for example, a Random Access Memory (RAM), a Read Only Memory (ROM), a Dynamic RAM (DRAM), a Synchronous DRAM (SD-RAM), a flash memory, a volatile memory, a non-volatile memory, a cache memory, a buffer, a short term memory unit, a long term memory unit, or other suitable memory units. Storage unit 195 may include, for example, a hard disk drive, a floppy disk drive, a Compact Disk (CD) drive, a CD-ROM drive, a DVD drive, or other suitable removable or non-removable storage units. Memory unit 194 and/or storage unit 195, for example, may store data processed by device 102.

In some demonstrative embodiments, device 102 may be configured to communicate with one or more other devices via a wireless and/or wired network 103.

In some demonstrative embodiments, network 103 may include a wired network, a local area network (LAN), a wireless LAN (WLAN) network, a radio network, a cellular network, a Wireless Fidelity (WiFi) network, an IR network, a Bluetooth (BT) network, and the like.

In some demonstrative embodiments, device 102 may allow one or more users to interact with one or more processes, applications and/or modules of device 102, e.g., as described herein.

In some demonstrative embodiments, device 102 may be configured to perform and/or to execute one or more operations, modules, processes, procedures and/or the like.

In some demonstrative embodiments, device 102 may be configured to determine a pupillary distance (PD) of a user of device 102, e.g., as described below.

In some demonstrative embodiments, the pupillary distance may include a near pupillary distance or a far pupillary distance.

In some demonstrative embodiments, system 100 may include at least one service, module, controller, and/or application 160 configured to determine the pupillary distance (PD) of the user of device 102, e.g., as described below.

In some demonstrative embodiments, application 160 may include, or may be implemented as, software, a software module, an application, a program, a subroutine, instructions, an instruction set, computing code, words, values, symbols, and the like.

In some demonstrative embodiments, application 160 may include a local application to be executed by device 102. For example, memory unit 194 and/or storage unit 195 may store instructions resulting in application 160, and/or processor 191 may be configured to execute the instructions resulting in application 160, e.g., as described below.

In other embodiments, application 160 may include a remote application to be executed by any suitable computing system, e.g., a server 170.

In some demonstrative embodiments, server 170 may include at least a remote server, a web-based server, a cloud server, and/or any other server.

In some demonstrative embodiments, the server 170 may include a suitable memory and/or storage unit 174 having stored thereon instructions resulting in application 160, and a suitable processor 171 to execute the instructions, e.g., as descried below.

In some demonstrative embodiments, application 160 may include a combination of a remote application and a local application.

In one example, application 160 may be downloaded and/or received by the user of device 102 from another computing system, e.g., server 170, such that application 160 may be executed locally by users of device 102. For example, the instructions may be received and stored, e.g., temporarily, in a memory or any suitable short-term memory or buffer of device 102, e.g., prior to being executed by processor 191 of device 102.

In another example, application 160 may include a front-end to be executed locally by device 102, and a backend to be executed by server 170. For example, one or more first operations of determining the pupillary distance of the user may be performed locally, for example, by device 102, and/or one or more second operations of determining the pupillary distance may be performed remotely, for example, by server 170, e.g., as described below.

In other embodiments, application 160 may include any other suitable computing arrangement and/or scheme.

In some demonstrative embodiments, system 100 may include an interface 110 to interface between a user of device 102 and one or more elements of system 100, e.g., application 160.

In some demonstrative embodiments, interface 110 may be implemented using any suitable hardware components and/or software components, for example, processors, controllers, memory units, storage units, input units, output units, communication units, operating systems, and/or applications.

In some embodiments, interface 110 may be implemented as part of any suitable module, system, device, or component of system 100.

In other embodiments, interface 110 may be implemented as a separate element of system 100.

In some demonstrative embodiments, interface 110 may be implemented as part of device 102. For example, interface 110 may be associated with and/or included as part of device 102.

In one example, interface 110 may be implemented, for example, as middleware, and/or as part of any suitable application of device 102. For example, interface 110 may be implemented as part of application 160 and/or as part of an OS of device 102.

In some demonstrative embodiments, interface 160 may be implemented as part of server 170. For example, interface 110 may be associated with and/or included as part of server 170.

In one example, interface 110 may include, or may be part of a Web-based application, a web-site, a web-page, a plug-in, an ActiveX control, a rich content component (e.g., a Flash or Shockwave component), or the like.

In some demonstrative embodiments, interface 110 may be associated with and/or may include, for example, a gateway (GW) 112 and/or an application programming interface (API) 114, for example, to communicate information and/or communications between elements of system 100 and/or to one or more other, e.g., internal or external, parties, users, applications and/or systems.

In some embodiments, interface 110 may include any suitable Graphic-User-Interface (GUI) 116 and/or any other suitable interface.

In some demonstrative embodiments, application 160 may be configured to determine the pupillary distance of the user based on a captured image of the user, e.g., as described below.

In some demonstrative embodiments, the captured image may be captured by the user, and may include the eyes of the user, e.g., as described below.

In one example, extracting a precise PD measurement from a two dimensional (2D) captured image, may include measuring, evaluating and/or analyzing one or more parameters to determine a three dimensional (3D) environment, for example, to determine the PD. For example, the 3D environment may reflect a camera located at a distance from a face of the user, and a location of each pupil of the user while looking at the camera, which may be in an offset from the center of the pupil, e.g., an offset of up to 1 millimeter. The location of the pupil may coincide with the line of sight of the user, e.g., at a visual axis.

In some demonstrative embodiments, device 102 may include an image capturing device, e.g., a camera 118 or any other device, configured to capture the image.

In some demonstrative embodiments, device 102 may include a light source 122 configured to illuminate the user, for example, when the image is captured.

In some demonstrative embodiments, light source 122 may include a flash, a LED light, or any other source of light.

In some demonstrative embodiments, application 160 may be configured to receive the captured image of the user, e.g., from the camera 118.

In some demonstrative embodiments, the captured image may include first and second reflections of a light of the light source 122.

In some demonstrative embodiments, the first reflection may include a reflection of the light from a first pupil of the user, e.g., a first Purkinje image from the first pupil, and the second reflection may include a reflection of the light from a second pupil of the user, e.g., a first Purkinje image from the second pupil).

In some demonstrative embodiments, application 160 may be configured to determine the pupillary distance of the user, for example, based on locations of the first and second reflections in the captured image, and an estimated distance between device 102 and the pupils of the user, e.g., when the image is captured.

In some demonstrative embodiments, application 160 may be configured to determine the pupillary distance of the user, for example, based on a number of pixels between the first and second reflections, and a pixel to millimeter (mm) ratio of the pixels, e.g., as described below.

In some demonstrative embodiments, application 160 may be configured to determine the pupillary distance of the user, for example, based on one or more attributes of camera 118, e.g., as described below.

In some demonstrative embodiments, application 160 may be configured to determine the pupillary distance of the user, for example, based on an eye radius parameter, and a distance between camera 118 and a plane including the pupils of the user, e.g., as described below.

In some demonstrative embodiments, application 160 may be configured to determine the pupillary distance of the user, for example, based on orientation information with respect to an orientation of device 102, for example, if device 102 is tilted, e.g., as described below.

In some demonstrative embodiments, application 160 may receive the captured image including the first and second reflections from the first and second pupils of the user.

In one example, application 160 may be configured to determine the PD locally, for example, if application 160 is locally implemented by device 102. According to this example, camera 118 may be configured to capture the image, and application 160 may be configured to receive the captured image, e.g., from camera 118, to determine the estimated distance between device 102 and the pupils of the user, and to determine the pupillary distance of the user, e.g., as described below.

In another example, application 160 may be configured to determine the PD remotely, for example, if application 160 is implemented by server 170, or if the back-end of application 160 is implemented by server 170, e.g., while the front-end of application 160 is implemented by device 102. According to this example, camera 118 may be configured to capture the image; the front-end of application 160 may be configured to receive the captured image, and to determine the estimated distance between device 102 and the pupils of the user; and server 170 and/or the back-end of application 160 may be configured to determine the pupillary distance of the user, e.g., based on information received from the front-end of application 160.

In one example, device 102 and/or the front-end of application 160 may be configured to send the captured image and the estimated distance to server 170, e.g., via network 103; and/or server 170 and/or the back-end of application 160 may be configured to receive the captured image and/or the estimated distance, and to determine the pupillary distance of the user, for example, based on the captured image and the estimated distance received from device 102.

In some demonstrative embodiments, the captured image may include an object on a face of the user ("the reference object").

In one example, the PD may be extracted from a single image of a person looking at the flash of the camera 118, for example, while the camera 118 captures the image, and the person is holding an object of a known size close to a feature of the face of the person.

In some demonstrative embodiments, application 160 may be configured to determine an estimated distance between camera 118 and the reference object, for example, based on one or more dimensions of the object on the face of the user, e.g., as described below.

In some demonstrative embodiments, application 160 may be configured to determine the estimated distance between camera 118 and the reference object, for example, based on acceleration information indicating an acceleration of device 102, e.g., as described below.

In some demonstrative embodiments, application 160 may be configured to determine the estimated distance between camera 118 and the reference object, for example, based on the object on the face of the user and one or more attributes of the camera 118, e.g., as described below.

In some demonstrative embodiments, the one or more attributes of camera 118 may include an Effective Focal Length (EFL) of a lens of the camera 118, a horizontal Field of View (FOV) of a sensor of the camera 118, a vertical field of view of the sensor of camera 118, a resolution of the sensor, a distance ("a sensor pitch") between two adjacent pixels of the sensor, and/or any other additional or alternative attributes of camera 118.

Figure 2:
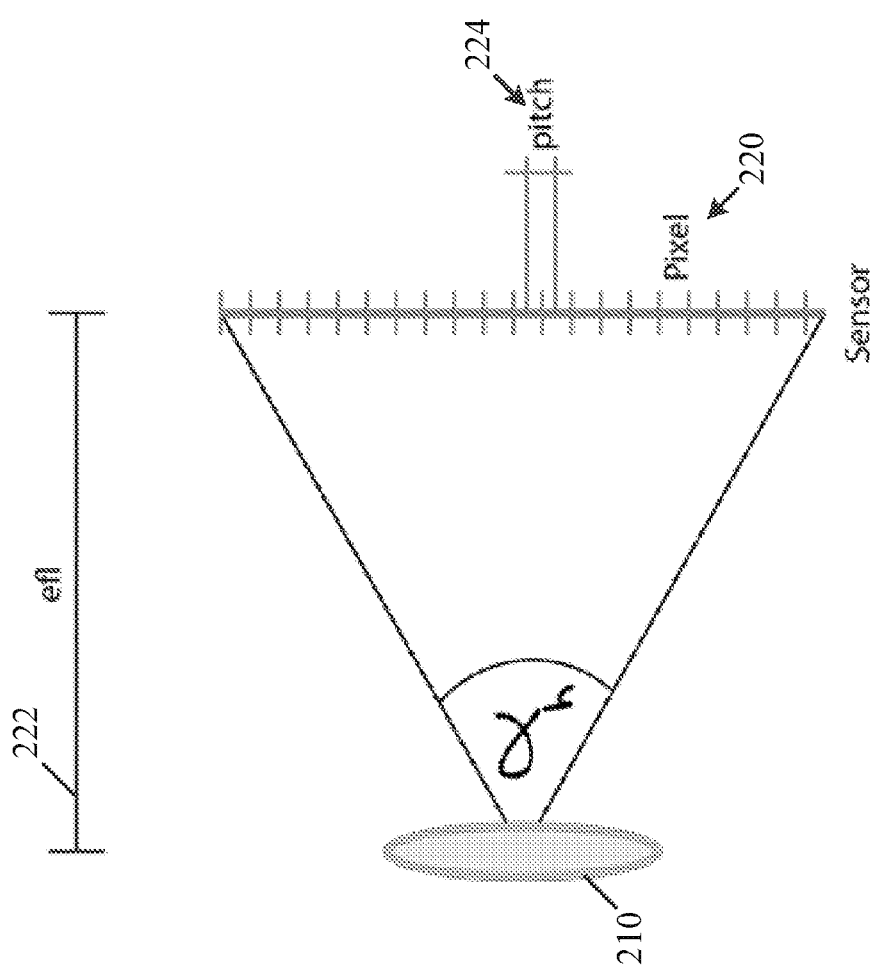
FIG. 2 is a schematic illustration of a lens and a sensor of a camera, in accordance with some demonstrative embodiments.

Reference is made to FIG. 2, which schematically illustrates a lens 210 and a sensor 220 of a camera, in accordance with some demonstrative embodiments. For example, camera 118 (FIG. 1) may include lens 210 and sensor 220.

In some demonstrative embodiments, as shown in FIG. 2, the lens 210 may have an EFL 222, which may be given and/or calibrated, e.g., by device 102 (FIG. 1), located at a distance equal to the lens EFL from the sensor 220.

In some demonstrative embodiments, a viewing horizontal angle, denoted $\alpha_h$, may be determined based on the horizontal size of the sensor 220, and the EFL 222 of the lens 210.

In some demonstrative embodiments, a viewing vertical angle may be determined, for example, based on the vertical size of the sensor 220.

In some demonstrative embodiments, as shown in FIG. 2, a sensor horizontal pitch 224, denoted $pitch_h$, may be defined as a distance between the centers of each two adjacent pixels.

In some demonstrative embodiments, the sensor pitch 224 may be determined, for example, based on the horizontal length of the sensor and the total number of horizontal pixels of the senor.

In some demonstrative embodiments, the sensor pitch 224 may be determined, for example, based on the EFL 222, the viewing horizontal angle $\alpha_h$, and/or the viewing vertical angle, e.g., as follows:

$$pitch_h = \frac{\text{sensor horizontal length}}{\text{total horizontal pixels}} = \frac{2*efl*\tan\left(\frac{\alpha_h}{2}\right)}{pixels_h} \quad (1)$$

Referring back to FIG. 1, in some demonstrative embodiments, application 160 may be configured to determine the estimated distance between camera 118 and the reference object, for example, based on the one or more attributes of camera 118, e.g., the viewing horizontal angle $\alpha_h$, EFL 222 (FIG. 2), and/or the sensor pitch 224 (FIG. 2), e.g., as described below.

In some demonstrative embodiments, application 160 may be configured to determine the estimated distance between camera 118 and the reference object, for example, based on the one or more attributes of camera 118, and the one or more dimensions of the reference object, e.g., as described below.

In some demonstrative embodiments, the reference object may include an object having one or more known dimensions, e.g., which may be measured and/or given. For example, the reference object may include a credit card, a banknote, and/or the like.

In some demonstrative embodiments, the reference object may include a facial object or element having one or more known dimensions, e.g., which may be measured and/or given. For example, the reference object may include an iris, an eye radius parameter, and/or the like.

In some demonstrative embodiments, camera 118 may be configured to capture the image including the reference object.

In some demonstrative embodiments, application 160 may be configured to determine the estimated distance between camera 118 and the reference object, for example, based on the imaged dimensions of the object in the captured image, the real dimensions of the object, and the camera attributes, e.g., as described below.

Figure 3:
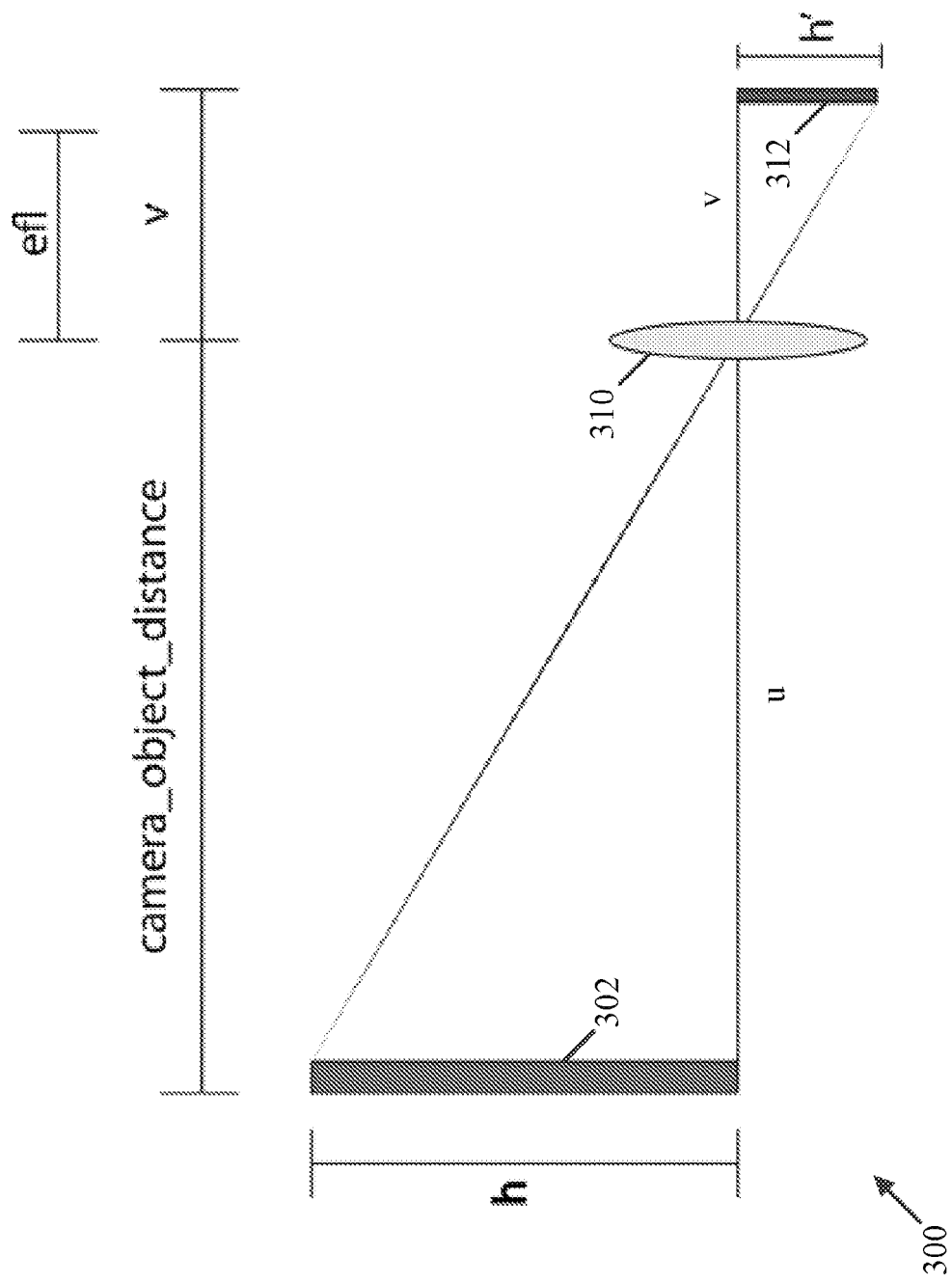
FIG. 3 is a schematic illustration of an imaging diagram for capturing an image of an object, in accordance with some demonstrative embodiments.

Reference is made to FIG. 3, which schematically illustrates an imaging diagram 300 for capturing an image of an object 302, in accordance with some demonstrative embodiments.

In some demonstrative embodiments, as shown in FIG. 3, an image 312 of object 302 may be captured via a lens 310 of a camera. For example, camera 118 (FIG. 1) may include lens 310.

In some demonstrative embodiments, as shown in FIG. 3, object 302 may have a height, denoted h, which may be known and/or given.

In some demonstrative embodiments, as shown in FIG. 3, image 312 of the object 302, e.g., when captured via lens 310, may have an imaged height, denoted h'.

In some demonstrative embodiments, a distance, denoted u, between lens 310 and the object 302 may be determined, for example, based on the EFL of lens 310, which may be known and/or given, the height h, and/or the imaged height h', e.g., as described below.

In some demonstrative embodiments, the following Equation may be given, for example, based on triangles similarity in imaging scheme 300, e.g., as follows:

$$\frac{h'}{h} = \frac{v}{u} \cong \frac{efl}{u} \quad (2)$$

wherein v is approximately the EFL of lens 310.

In some demonstrative embodiments, the imaged height h' of image 312 may be based on a number of pixels, denoted h'_pixels_estimated, occupied by image 312, and a sensor pitch, denoted pitch, of lens 310, e.g., as follows:

$$h'=pitch*h'\_pixels\_estimated \quad (3)$$

In some demonstrative embodiments, the distance u may be determined, for example, based on Equation 2 and Equation 3, e.g., as follows:

$$u \cong \frac{efl*h}{h'} = \frac{efl}{pitch} * \frac{h}{h\_pixels\_estimated} \quad (4)$$

In some demonstrative embodiments, as shown in FIG. 3, object 302 may be vertical, e.g., with no tilt.

In some demonstrative embodiments, an object to be captured by the camera may be tilted, e.g., as described below with reference to FIG. 4.

Figure 4:
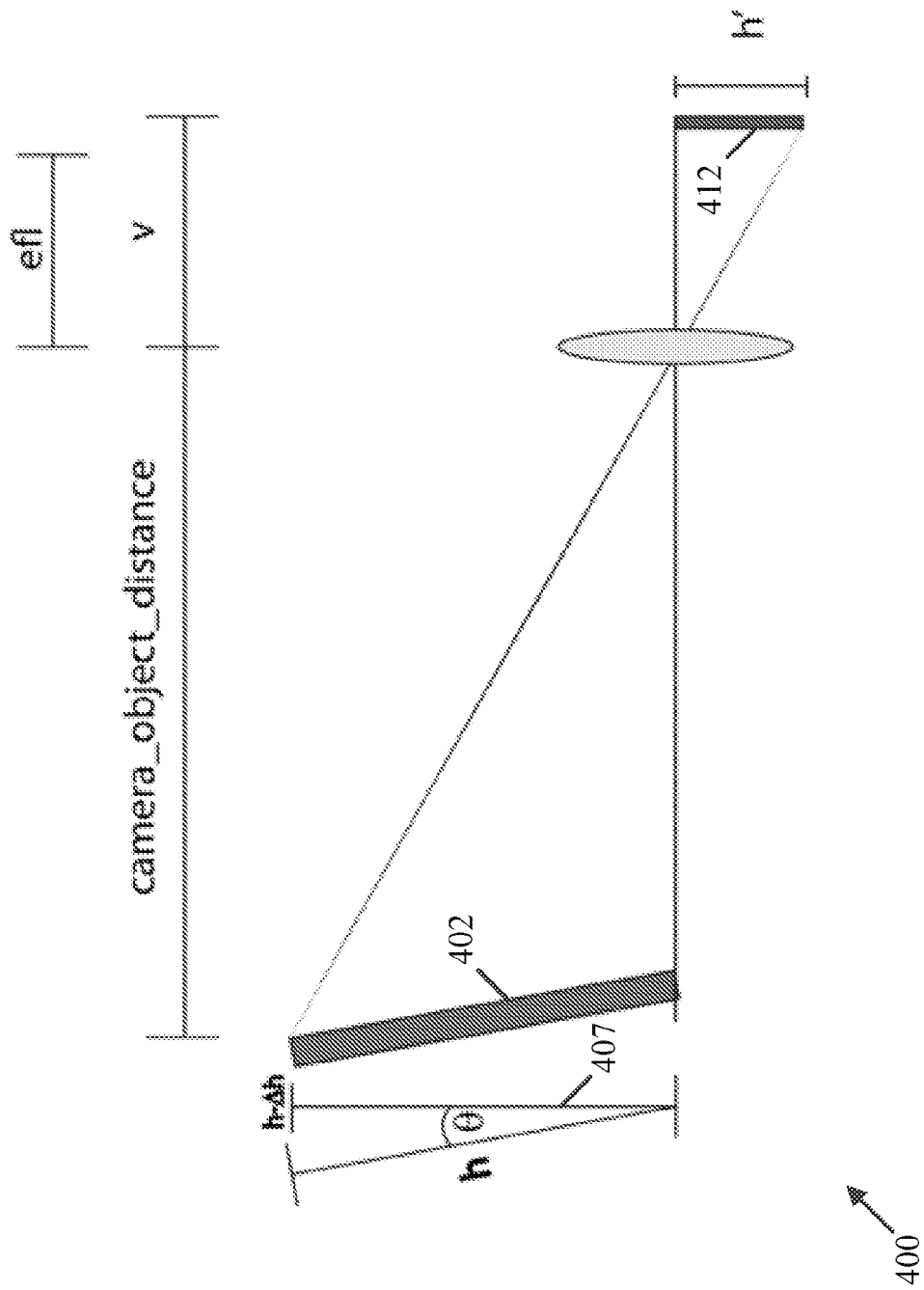
FIG. 4 is a schematic illustration of an imaging diagram for capturing an image of a tilted object, in accordance with some demonstrative embodiments.

Reference is made to FIG. 4, which schematically illustrates an imaging diagram 400 for capturing an image of a tilted object 402, in accordance with some demonstrative embodiments.

In some demonstrative embodiments, as shown in FIG. 4, an image 412 of tilted object 402 may be captured via a lens 410 of a camera. For example, camera 118 (FIG. 1) may include lens 410.

In some demonstrative embodiments, as shown in FIG. 4, object 402 may have a height, denoted h, which may be known and/or given.

In some demonstrative embodiments, as shown in FIG. 4, an image 412 of the object 402, e.g., when captured via lens 410, may have an imaged height, denoted h'.

In some demonstrative embodiments, as shown in FIG. 4, the imaged height h' of the image 412 may reflect a projection of object 402 onto a plane 407 at a tilt angle, denoted θ.

In some demonstrative embodiments, as shown in FIG. 4, the projection of height h may result in an error and/or a reduction, denoted Δh, of the height h of object 402, which may reduce the imaged height h' of the image 412.

In some demonstrative embodiments, the error Δh in the object size h may be determined, e.g., as follows:

$$\Delta h = h*(1-\cos(\theta)) \quad (5)$$

In one example, for an assumed error Δh, which may result, for example, from a tilt angle of ±10° (degrees), a relative error of the height may be of approximately, e.g., +1.5% (percent).

In some demonstrative embodiments, the relative error may affect the estimated distance, for example, by the same percentage.

Referring back to FIG. 1, in some demonstrative embodiments, application 160 may be configured to determine the estimated distance between camera 118 and the object, for example, based on a 3D Cartesian coordinate of the object, e.g., as described below.

In some demonstrative embodiments, device 102 may include a 3D sensor 124 configured to determine the 3D Cartesian coordinate of the object.

In some demonstrative embodiments, 3D sensor 124 may be configured to map the object to a set of points, e.g., 3 points, denoted $\{x_i, y_i, z_i\}$, e.g., in a 3 dimension Cartesian coordinate.

In one example, the set of points may include a projected structure, including a distance dependent structure, a distance from defocus structure, a stereo-based triangulation structure, and/or the like.

In some demonstrative embodiments, a distance, denoted d, between the object and camera 118 may be determined, e.g., as follows:

$$d = \sqrt{(x_k-x_0)^2+(y_k-y_0)^2+(z_k-z_0)^2} \quad (6)$$

wherein $\{x_0, y_0, z_0\}$ denotes the camera location, e.g., in the same Cartesian coordinate system as the object, and k denotes a discrete point on the object, which was captured by the 3D sensor 124.

In some demonstrative embodiments, application 160 may be configured to estimate the distance from the camera to the object, for example, based on information from the 3D sensor 124.

In some demonstrative embodiments, 3D sensor 124 may be configured to provide information describing each pixel in an image or each group of pixels in the image as a function of distance from the camera, or as a function of absolute dimension, e.g., in meters, inches or any other size units.

In one example, the function of distance may enable application 160 to determine the distance between the object and camera 118.

In another example, the function of absolute dimension may enable to determine a distance to an object, for example, based on Equation 4. In one example, application 160 may determine the object size h, for example, based on the information from 3D sensor 124, for example, by an estimation of how many pixels the imaged height of the object acquired in the image.

In some demonstrative embodiments, application 160 may be configured to determine the distance between the camera 118 and the eye of the user, e.g., even without using the object, for example, by using acceleration information corresponding to the acceleration of device 102, e.g., as described below.

In some demonstrative embodiments, application 160 may be configured to determine the estimated distance between the camera 118 and the eyes of the user, for example, based on the acceleration information indicating the acceleration of device 102, e.g., as described below.

In some demonstrative embodiments, device 102 may include an accelerometer 126 to provide to application 160 the acceleration information of device 102.

In some demonstrative embodiments, accelerometer 126 may be configured to provide the acceleration information at a given time, for example, for each axis, e.g., of the Cartesian coordinate system.

In some demonstrative embodiments, application 160 may be configured to determine the distance between the camera 118 and the eyes of the user, for example, based on satisfaction of a set of two conditions, e.g., as described below.

In some demonstrative embodiments, application 160 may determine the distance between the camera 118 and the eyes of the user, for example, after performing an initialization procedure, which may include setting an initial distance, denoted $x_0$, between the eye of the user and the camera 118, when holding device 102 close to the eye of the user.

In some demonstrative embodiments, application 160 may cause device 102 to instruct the user to begin the measurement for the distance between the camera 118 and the eyes of the user, for example, after the initialization procedure, by instructing the user to move the device 102 away from the eyes.

In some demonstrative embodiments, application 160 may receive from accelerometer 126 the acceleration information of device 102, e.g., in one or more, e.g., all, axes of the Cartesian coordinate system, for example, according to the movement of device 102.

In some demonstrative embodiments, application 160 may determine an x-axis distance on the X-axis, denoted x(t'), at a given time, for example, based on acceleration information on the X-axis, denoted $a_x(t)$, at the given time, e.g., as follows:

$$v_x(t') = \int_0^{t'} a_x(t)dtx(t') = \int_0^{t'} v_x(t)dt = \quad (7)$$

$$\int\int_0^{t'} a_x(t)dt = \int\int a_x(t)dt - \int\int a_x(0)dt = \int\int a_x(t)dt - x0$$

In some demonstrative embodiments, application 160 may determine the x-axis distance x(t'), for example, based on a velocity, denoted $v_x(t')$ of device 102 at the given time, e.g., as follows:

$$v_x(t') = \int_0^{t'} a_x(t)dt \quad (8)$$

In some demonstrative embodiments, application 160 may determine a Y-axis distance on the Y-axis, denoted y(t'), for example, based on acceleration, denoted $a_y(t)$, of device 102 on the Y-axis, e.g., in a similar manner to determining the distance x(t').

In some demonstrative embodiments, application 160 may determine a Z-axis distance on the Z-axis, denoted z(t'), for example, based on acceleration, denoted $a_z(t)$, of device 102 on the Z-axis, e.g., in a similar manner to determining the distance x(t').

In some demonstrative embodiments, application 160 may determine the estimated distance, denoted r(t'), of the camera 118 from the eye, for example, based on the X-axis distance, the Y-axis distance, and the Z-axis distance, e.g., as follows:

$$r(t') = \sqrt{x(t')^2+y(t')^2+z(t')^2} \quad (9)$$

In some demonstrative embodiments, an accuracy of the estimated distance r(t') may be increased, for example, by using more than one measurement to estimate the distance, e.g., as described below.

In some demonstrative embodiments, application 160 may be configured to use the acceleration information in combination with information from other distance metering sensors, for example, to increase the metering range, reliability, accuracy and/or sensitivity.

In some demonstrative embodiments, application 160 may be configured to increase an accuracy of the distance estimation by accelerometer 126, for example, by integrating one or more images captured by camera 118, for example, in addition to the acceleration information.

In some demonstrative embodiments, application 160 may be configured to control, cause, trigger, and/or instruct camera 118 to capture one or more images, for example, during the movement of device 102, e.g., after the initialization procedure.

In some demonstrative embodiments, application 160 may be configured to use information from the captured images, for example, to increase the accuracy of the estimated distance, e.g., based on the acceleration information.

In some demonstrative embodiments, application 160 may use the information from the captured images, for example, when the captured images include an object, which has known dimensions, e.g., as described above.

In some demonstrative embodiments, application 160 may be configured to determine a distance between a pair of images of the captured images, for example, based on a change in magnification of the object.

In some demonstrative embodiments, an error of the accelerometer information may not be accumulated throughout the movement of device 102, for example, if the distance between the pair of images is used to evaluate the acceleration information.

In one example, the initialization procedure may be performed at a time, denoted $t'_0$, followed by N camera acquisitions at times, denoted $\{t'_1, t'_2, t'_3, t'_4 \ldots t'_N\}$, and at distances, denoted $\{r'_1, r'_2, r'_3, r'_4 \ldots r'_N\}$, determined from the accelerometer information sensor data, and the related sizes, denoted $\{h'_1, h'_2, h'_3, h'_4 \ldots h'_N\}$, of the object at the captured images.

In some demonstrative embodiments, an optimization for the distance measurements related to the accelerometer information may be performed to reduce the error of the accelerator information, for example, when all the captured correspond to the same size h of the object.

In some demonstrative embodiments, an equation to optimize the minimum error may be defined, e.g., as follows:

$$\min\left(\sum_{n=1}^{N}\left[\frac{\{r'_1, r'_2, r'_3, r'_4 \ldots r'_N\} - \frac{efl}{pitch} * h}{\{h'_1, h'_2, h'_3, h'_4 \ldots h'_N\}\_\text{pixels\_estimated}}\right]^2\right) \quad (10)$$

In some demonstrative embodiments, application 160 may be configured to determine a distance between a plane of the pupils of the user ("the pupils plane") and the camera 118, for example, to determine the pupillary distance of the user.

In some demonstrative embodiments, application 160 may determine the distance between the pupils plane and camera 118, for example, after determining the distance from the camera 118 to the object, for example, using 3D sensor 124, accelerometer 126, and/or the captured images including the object, e.g., as described above.

In some demonstrative embodiments, calculating the distance between the pupils plane and camera 118 may enable determining a magnification at the pupils plane, which may enable to calculate the absolute distance between the pupils.

In some demonstrative embodiments, calculating the distance between the pupils plane and camera 118 may enable determining an angle at which the eyes were looking to the camera, for example, to accommodate for the eye convergence when looking to camera 118.

In some demonstrative embodiments, assuming that camera 118 accommodates for distortion aberration created from a flat sensor and non-optimal lens, the magnification across a plane perpendicular to the sensor, or the lens apex, of camera 118, may be uniform, and pincushion and barrel distortions may be minimal.

In some demonstrative embodiments, a magnification, denoted $M_{object}$(camera_object_distnace), may define a conversion between an estimated number of pixels, denoted $h_{obj}'\_$pixels_estimated, of a captured dimension, denoted $h'_{obj}$, of the object at the captured image at a plain perpendicular to the sensor of camera 118, and an absolute dimension of the object, denoted $h_{obj}$, at a plain including the object.

In some demonstrative embodiments, determining the magnification may enable determining a pixel to millimeter ratio, which may enable calculating the PD from the captured image, for example, by calculating a number of pixels, e.g., as descried below.

In one example, it may be assumed that camera 118 may be tilted, and one or more features in the captured image may be at different distances from the camera 118. According to this example, each set of pixels in the captured image may represent a different magnification.

In some demonstrative embodiments, the magnification may be based on the distance between camera 118 and the object, e.g., as follows:

$$M_{object}(\text{camera\_object\_distance}) = \frac{v}{\text{camera\_object\_distance}} \cong \frac{efl}{\text{camera\_object\_distance}} \quad (11)$$

In some demonstrative embodiments, the absolute dimension, e.g., height $h_{obj}$, of the object may be determined based on the magnification and the imaged dimension, e.g., the imaged height, $h'_{obj}$, e.g., as followed:

$$h_{obj} = h'_{obj} * M_{object}(\text{camera\_object\_distance}) == \quad (12)$$

$$h'_{obj}\_\text{pixels\_estimated} * pitch * M_{object}(\text{camera\_object\_distance})$$

In some demonstrative embodiments, the object may not be positioned on the plane of the pupils. For example, the object may be positioned on a forehead of the user.

In some demonstrative embodiments, application 160 may be configured to determine a change of magnification between an object plane, which includes the object, and the pupils plane, while considering the tilt of the acquiring camera 118.

In some demonstrative embodiments, application 160 may determine the distance between a plane of the pupils of the user and the camera 118, for example, based on an axial offset between the object and the pupils along an axis perpendicular to a plane including the object, for example, the object plane, e.g., as described below.

In some demonstrative embodiments, application 160 may be configured to determine the axial offset between the object and the pupils along the axis perpendicular to the plane including the object, e.g., as described below.

In some demonstrative embodiments, calculating the axial offset may enable determining the magnification change between the object plane and the pupils plane.

In some demonstrative embodiments, application 160 may be configured to determine the change of magnification, while considering a tilt of camera 118.

In one example, camera 118 may not be vertical to the ground, for example, when capturing the image including the object.

In some demonstrative embodiments, application 160 may be configured to determine the distance between the pupils plane and the object plane, for example, based on the axial offset and the tilt of camera 180, e.g., as described below.

In some demonstrative embodiments, device 102 may include an orientation estimator 128, configured to determine an orientation of device 102, and/or an orientation of one or more elements of device 102, e.g., camera 118.

In some demonstrative embodiments, application 160 may be configured to receive, e.g., from orientation estimator 128, orientation information indicating an orientation of device 102, for example, when the image is captured.

In some demonstrative embodiments, application 160 may be configured to determine the pupillary distance of the user, for example, based on the orientation information.

In some demonstrative embodiments, the orientation information may indicate an orientation of camera 118.

In some demonstrative embodiments, the orientation information may indicate the tilt angle of camera 118.

In one example, application 160 may be configured to determine the tilt angle of camera 118, e.g., when the image is captured, for example, based on the orientation of camera 118 and/or the orientation of device 102.

In some demonstrative embodiments, application 160 may be configured to determine the pupillary distance of the user, for example, based on the orientation information and the axial offset between the object and the pupils along an axis perpendicular to a plane including the object, e.g., as described below.

Figure 5:
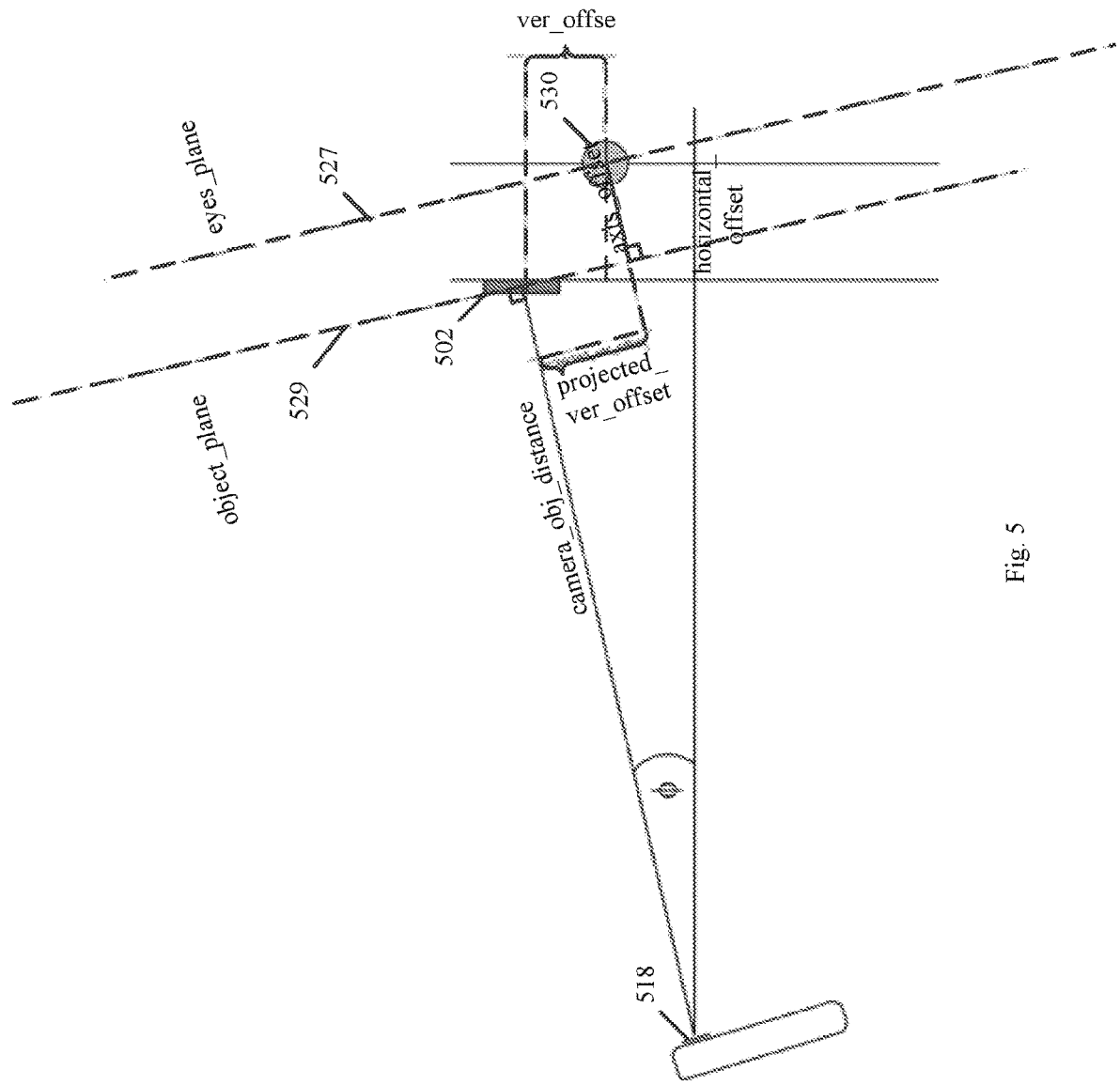
FIG. 5 is a schematic illustration of an imaging diagram for capturing an object by a tilted camera, in accordance with some demonstrative embodiments.

Reference is made to FIG. 5, which schematically illustrates a capturing diagram 500 for capturing of an object 502 by a tilted camera 518, in accordance with some demonstrative embodiments. For example, camera 518 may perform the functionality of camera 118 (FIG. 1).

In some demonstrative embodiments, as shown in FIG. 5, camera 518 may be tilted at a tilt angle, denoted θ, e.g., with respect to the horizon.

In some demonstrative embodiments, as shown in FIG. 5, camera 518 may be at a distance, denoted camera_obj_distance, from object 502.

In some demonstrative embodiments, as shown in FIG. 5, object 502 may be located at a horizontal offset, denoted, horizontal_offset, and a vertical offset, denoted ver_offset, from the eyes 506 of the user.

In some demonstrative embodiments, as shown in FIG. 5, eyes 530 may be included in a plane 527, denoted eyesplane, e.g., the pupils plane, which is perpendicular to the sensor of camera 118.

In some demonstrative embodiments, as shown in FIG. 5, object 502 may be included in a plane 529, denoted object_plane, which is perpendicular to the sensor of camera 118.

In some demonstrative embodiments, as shown in FIG. 5, there may be an axial offset, denoted axis_offset, on an axis perpendicular to the plane 527 and the plane 529.

In some demonstrative embodiments, as shown in FIG. 5, the axial offset, may define a distance between the plane 527 and the plane 529.

In some demonstrative embodiments, as shown in FIG. 5, there may be a vertical projected offset, denoted projected_ver_offset, between the centers of eyes 530 and object 502, when the centers of eyes 530 and object 502 are projected onto the plane 529 and/or the plane 527.

In some demonstrative embodiments, it may be assumed that the magnification of the captured image is uniform across planes perpendicular to the camera sensor, e.g., the plane 527 and/or the plane 529.

In some demonstrative embodiments, the axial offset may be determined based on the vertical projected offset, the horizontal offset, and the tilt angle, e.g., as follows:

$$\text{axis\_offset} = \frac{\text{horizontal\_offset} - \text{projected\_ver\_distance} * \sin(\theta)}{\cos(\theta)} \quad (13)$$

In some demonstrative embodiments, the vertical projected offset may be determined, for example, by analyzing a vertical displacement of the eyes 530 from the object 502 on the projected plane, e.g., the plane 529, for example, by estimating a number of pixels between the centers of camera 518 and eyes 530 at the captured image.

In some demonstrative embodiments, the horizontal offset may be given, calculated and/or may be predefined, e.g., approximately 30 millimeter (mm).

In some demonstrative embodiments, a magnification, denoted $M_{eyes}$, at the pupils plane, e.g., plane 527, may be based on the distance from camera 518 to the pupils plane.

In some demonstrative embodiments, the distance from camera 518 to the pupils plane may be based on a sum of the distance from the object to the camera 118, and the axial offset, e.g., as may be determined according to Equation 13.

In some demonstrative embodiments, a distance, denoted u, between the camera and the pupils plane may be defined based on a sum of the distance from the object to the camera 118, and the axial offset, e.g., as follows:

$$u = \text{camera\_object\_distance} + \text{axis\_offset} \quad (14)$$

In some demonstrative embodiments, a magnification, denoted $M_{eyes}(u)$, at the distance u may be determined e.g., as follows:

$$M_{eyes}(u) \cong \frac{efl}{\text{camera\_object\_distance} + \text{axis\_offset}} \quad (15)$$

Referring back to FIG. 1, in some demonstrative embodiments, application 160 may be configured to identify a location on the pupil, through which the user looks into camera 118, e.g., when capturing the image.

In some demonstrative embodiments, application 160 may be configured to identify the location on the pupil, through which the user looks into camera 118, for example, based on the reflection of light from the eye in the captured image, e.g., as described below.

In some demonstrative embodiments, application 160 may be configured to identify the location on the pupil, through which the user looks into camera 118, e.g., based on a first Purkinje image.

Figure 6:
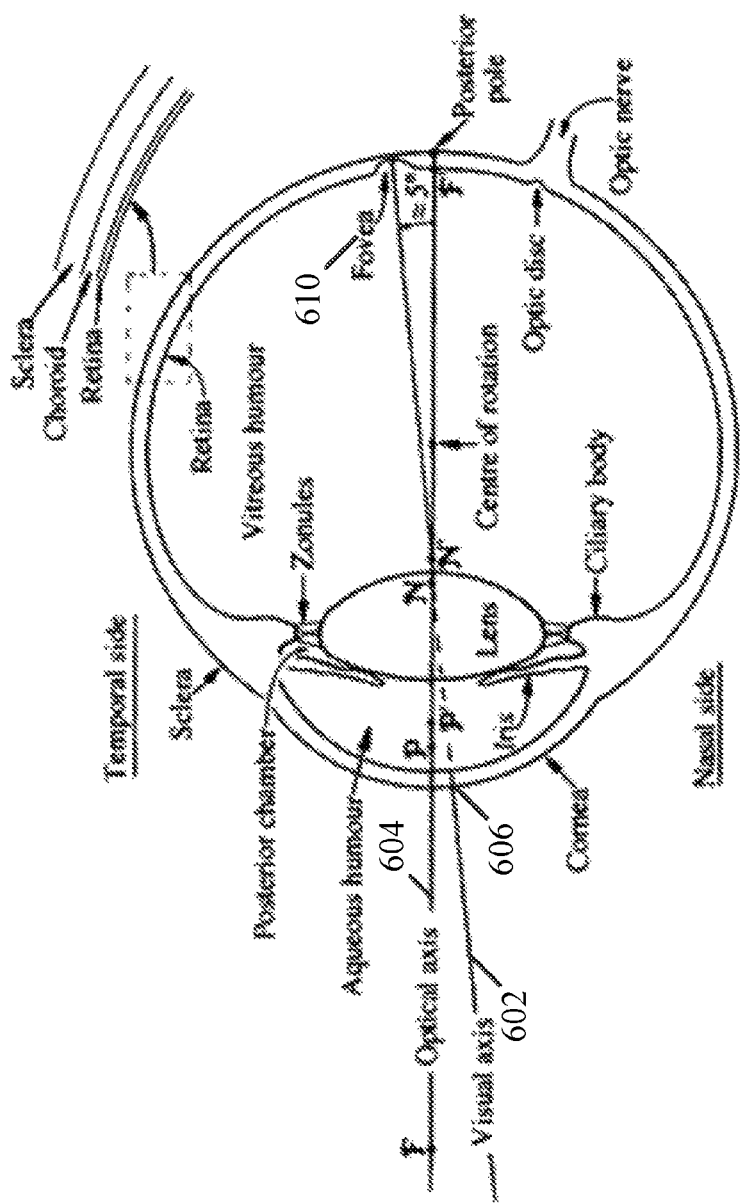
FIG. 6 is a schematic illustration of a horizontal section of a right eye of a user, in accordance with some demonstrative embodiments.

Reference is made to FIG. 6, which schematically illustrates a horizontal section of a right eye 600 of a user, in accordance with some demonstrative embodiments.

In some demonstrative embodiments, as shown in FIG. 6, the horizontal section of the right eye 600, may depict a difference between a visual axis 602 and an optical axis 604 of the right eye 600.

In some demonstrative embodiments, a location 606 in which the visual axis 602 crosses the pupil may be used to measure the PD, for example, since the eye 600 would rotate to view the most sharp image, e.g., of camera 118, that is imaged at the Fovea 610.

In some demonstrative embodiments, the Fovea 610, may be located about 5 degrees temporally, e.g., towards the ear, for example, when looking from above, to the optical axis 604. Therefore, the line of sight, in which the eye is rotated to look at the object, may not coincide with the optical axis 604, which connects the line between the cornea apex and the center of the pupil. Accordingly, the location 606 may not be the center of the pupil.

In some demonstrative embodiments, application 160 (FIG. 1) may be configured to identify location 606, for example, based on a reflection of the light source 122 on eye 600 at the captured image.

In one example, location 606 may be identified, for example, by looking for the first reflection, e.g., the first Purkinje image, which is the reflection of light source 122, imaged by the most outer reflecting cornea surface. The eye may be rotated to view the light source 122, and the reflecting cornea surface may be perpendicular to the light source 122. Therefore, the first reflection may be along the visual axis 602. Accordingly, location 606 may be determined based on the first reelection in the captured image.

In some demonstrative embodiments, application 160 (FIG. 1) may determine the PD, for example, based on location 606 of the right eye 600 and a location of the second reflection in the left eye, e.g., instead of using the center of the pupil or an arbitrary location in the pupil.

Referring back to FIG. 1, in some demonstrative embodiments, application 160 may be configured to determine a number of pixels, denoted heyes'_pixels_estimated, between the first and second reelections in the captured image, e.g., location 606 (FIG. 6) of the right eye 600 (FIG. 6), and the location of the second reflection of the left eye.

In some demonstrative embodiments, application 160 may be configured to calculate a PD, denoted PDconvergence, for converging eyes, for example, when the eyes are looking towards camera 118.

In some demonstrative embodiments, application 160 may calculate the PD for converging eyes, for example, based on the sensor pitch, and the magnification at the pupils plane and the number of pixels, e.g., as follows:

$$PD_{convergence} = h'_{eyes}\_pixels\_estimated * pitch / M_{eyes}(u) == \frac{h'_{eyes}\_pixels\_estimated * pitch *}{(camera\_object\_distance + axis\_offset)}{(efl)} \quad (16)$$

In some demonstrative embodiments, application 160 may be configured to calculate the PD, for example, when the eyes are looking towards infinity ("infinity eyes").

In some demonstrative embodiments, application 160 may be configured to calculate a correction between the pupillary distance for converging eyes and the pupillary distance for infinity eyes, e.g., as described below.

Figure 7:
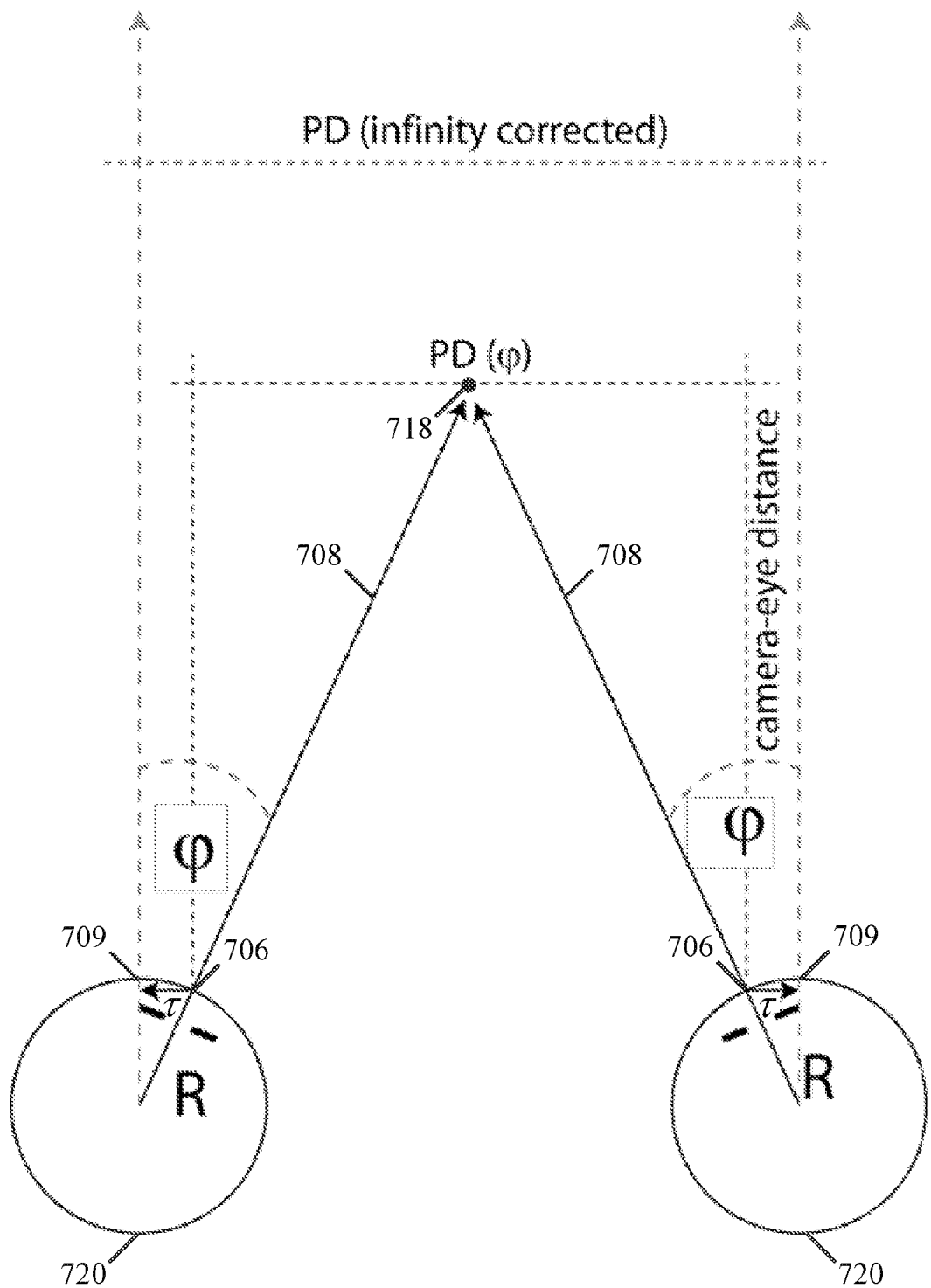
FIG. 7 is a schematic illustration of a pupillary distance between two eyes of a user looking towards a camera, in accordance with some demonstrative embodiments.

Reference is made to FIG. 7, which schematically illustrates a PD between two eyes 720 of a user looking towards a camera 718, in accordance with some demonstrative embodiments.

In some demonstrative embodiments, as shown in FIG. 7, camera 718 may be located at a distance, denoted camera_eye_distance, from the eyes 720.

In some demonstrative embodiments, as shown in FIG. 7, each eye 720 is rotated at an angle φ, e.g., towards the nose, to look at the camera 718.

In some demonstrative embodiments, as shown in FIG. 7, a location 706 of a visual axis 708 crossing the pupil may be displaced transversely at an accommodation distance, denoted τ, towards a location 709, e.g., towards the ears, for example, when eyes 720 look toward infinity.

In some demonstrative embodiments, the accommodation distance τ may be, for example, the result of eyes 730 rotating at a radius, denoted R, at the angle φ, to the location 709, e.g., to look towards infinity.

In some demonstrative embodiments, assuming that the centers of rotation of eyes 720 are equal, the radiuses R of the eyes may be equal to a predefined value, e.g., of about 13.5 mm.

In some demonstrative embodiments, locations 709 may be considered, for example, when determining the pupillary distance, e.g., for distance spectacles.

In some demonstrative embodiments, as shown in FIG. 7, the pupillary distance for converging eyes, denoted PD(φ), may be defined, for example, when eyes 720 are converged to look toward a flash of camera 718, for example, if camera 718 is located at a e, which is not an infinity distance, e.g., the distance camera_eye_distance.

In some demonstrative embodiments, the angle φ may be expressed as follows:

$$\varphi = \tan^{-1}\left(\frac{PD_{convergence}/2}{camera\_eye\_distance}\right) \quad (17)$$

In some demonstrative embodiments, the pupillary distance for infinity eyes, denoted PDinfinity, e.g., when eyes 720 are looking to infinity, may be determined, for example, based on the sum of the pupillary distance PDconvergence for converging eyes and the accommodation distance τ for the two eyes 720, e.g., as follows:

$$PD = P_{convergence} + 2\tau = PD_{convergence} + 2R\sin(\varphi) \quad (18)$$

In some demonstrative embodiments, the pupillary distance PDinfinity may be determined, for example, by combining Equation 17 and Equation 18, e.g., as follows:

$$PD_{infinity} = PD_{convergence}\left(1 + \frac{R}{camera\_eye\_distance}\right) \quad (19)$$

In some demonstrative embodiments, a negative feedback may reduce an accumulated error. For example, in a case when a calculated horizontal offset horizontal_offset is longer than a real horizontal offset, e.g., between the eye and the object, the distance camera_eye_distance may be longer, e.g., resulting with a higher PD in the eyes plane. However, the accommodation for conversion, e.g., the distance τ, from higher distance, e.g., may reduce angle φ, which may result in a lower addition to the pupillary distance, which may reduce the accumulated error.

Reference is made to FIGS. 8A-8F, which schematically illustrate histograms of Monte Carlo simulations, in accordance with some demonstrative embodiments.

In some demonstrative embodiments, the simulations considered variations in a distance between the camera to the object, e.g., between 300 mm and 900 mm, an error in camera to object distance estimation, e.g., between −5 mm and 15 mm, and a horizontal offset error between the pupils and the object, e.g., between −15 mm and 5 mm.

Figure 8A:
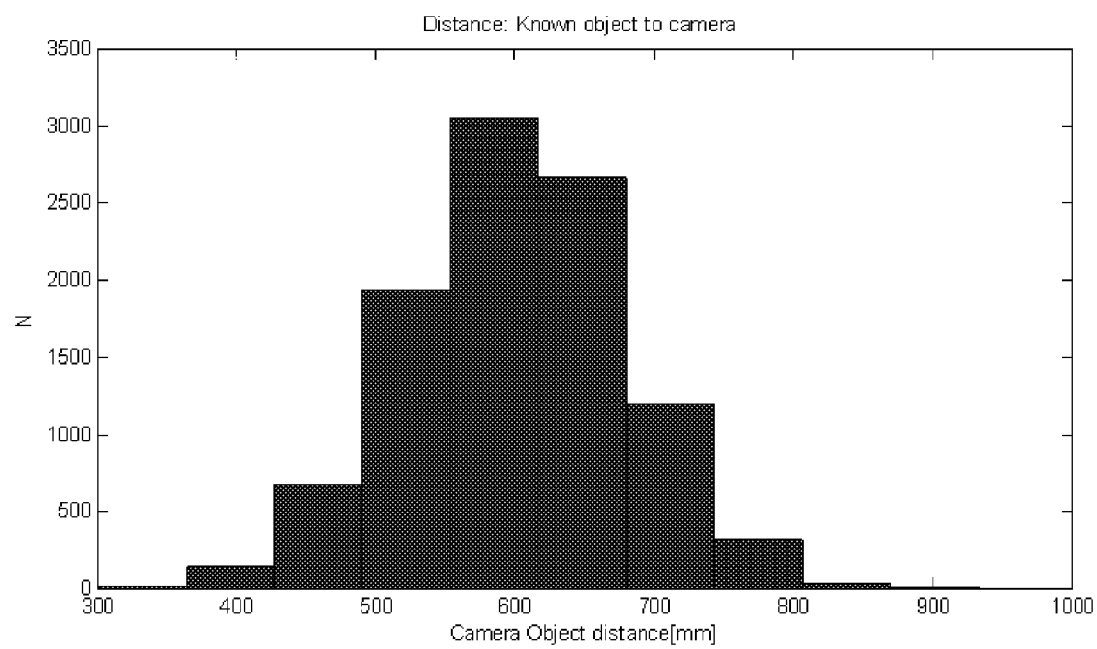
FIGS. 8A-8F are schematic illustrations of histograms corresponding to a plurality of Monte Carlo simulations, in accordance with some demonstrative embodiments.

In some demonstrative embodiments, FIG. 8A shows a histogram of Monte Carlo simulations to evaluate the accumulated errors generated from a camera error to known size object estimation, for example, when the camera is placed at multiple distances.

Figure 8B:
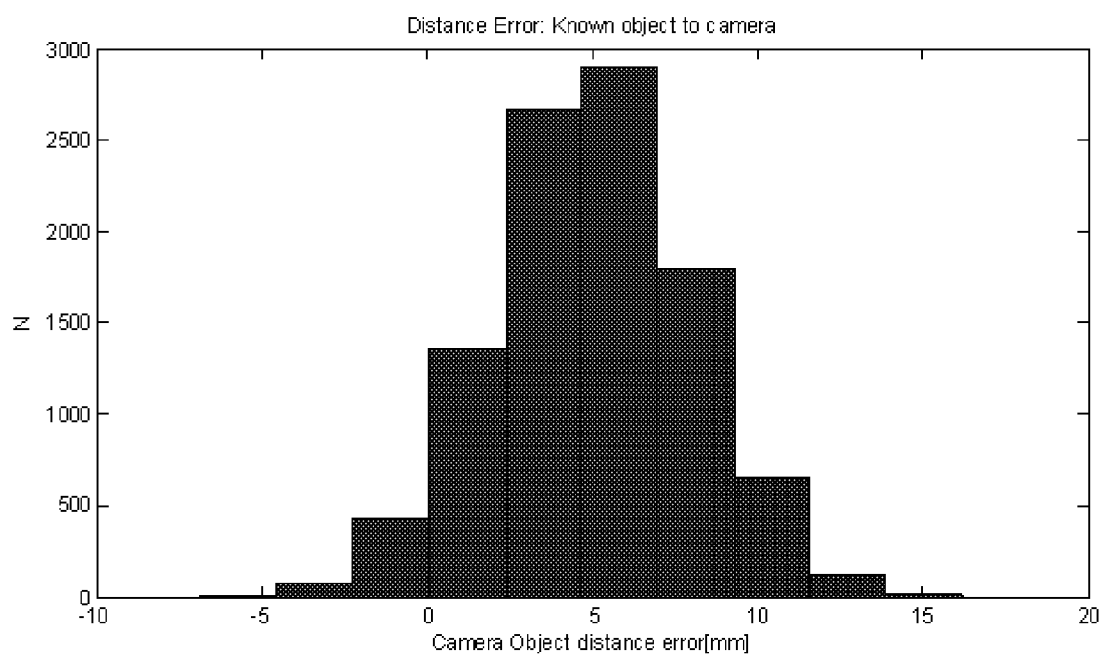

In some demonstrative embodiments, FIG. 8B shows a histogram of Monte Carlo simulations to evaluate the accumulated errors generated from an error to the camera to a known size object estimation.

Figure 8C:
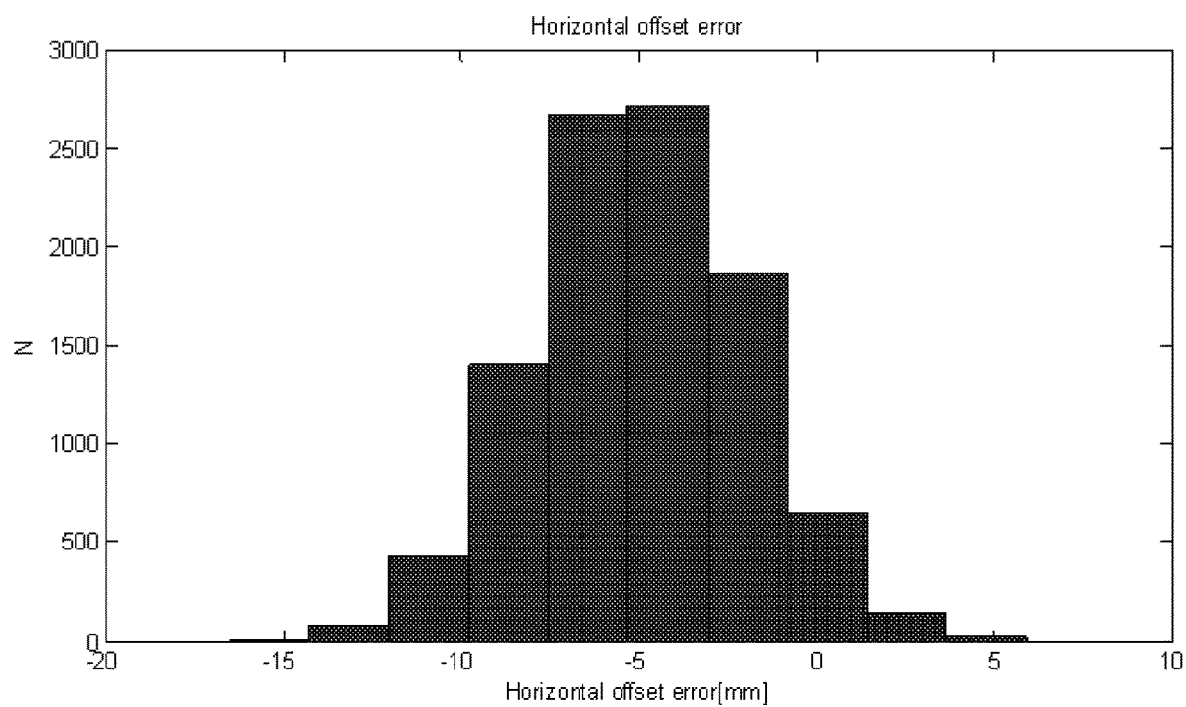

In some demonstrative embodiments, FIG. 8C shows a histogram of Monte Carlo simulations to evaluate the error of a horizontal offset between the pupils and the object.

Figure 8D:
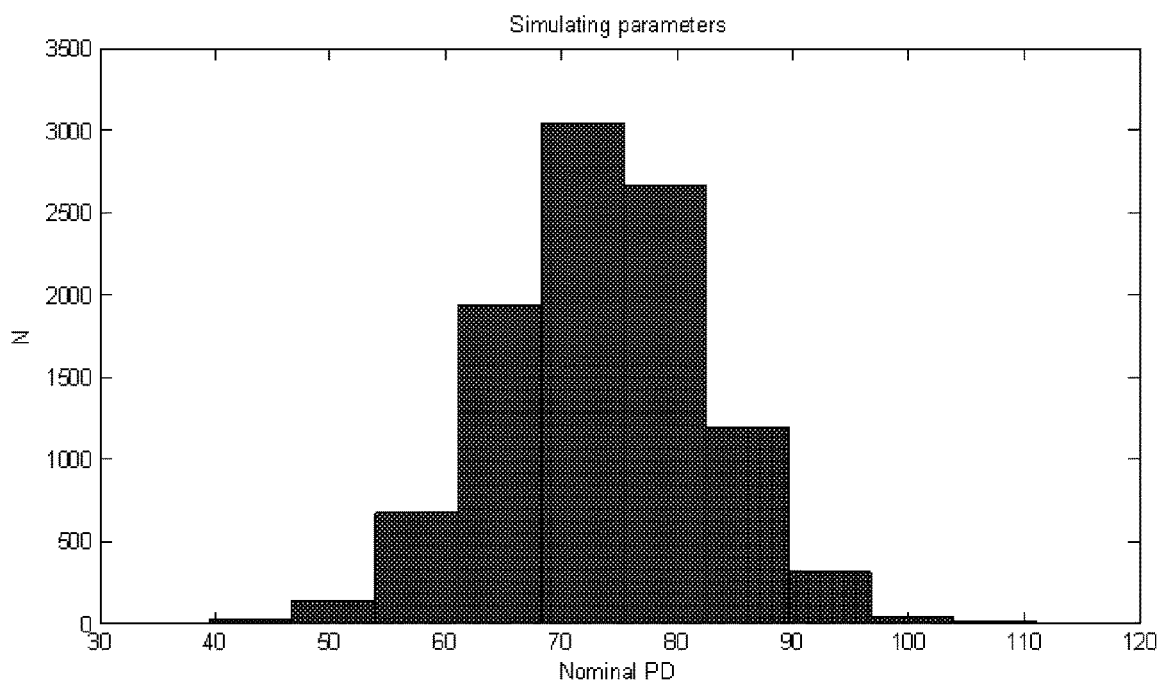

In some demonstrative embodiments, FIG. 8D shows a histogram of Monte Carlo simulations to depict a variation of the nominal PD.

Figure 8E:
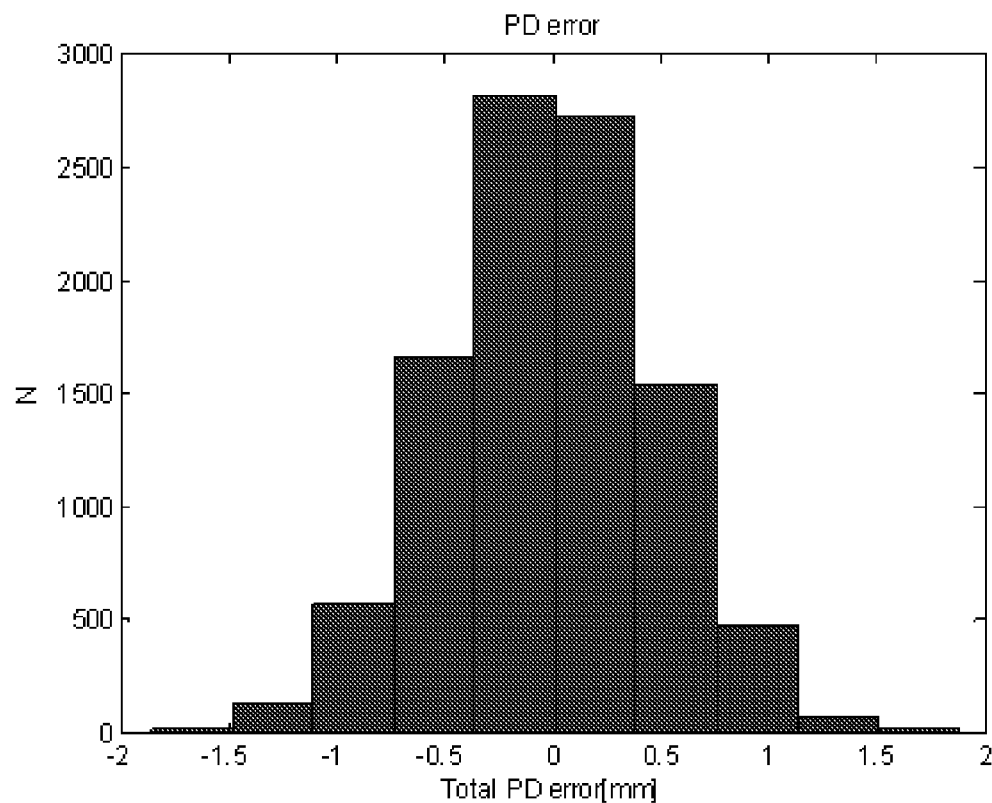

In some demonstrative embodiments, FIG. 8E shows the result of an accumulated error of the horizontal axis presented as a histogram.

In some demonstrative embodiments, the horizontal axis of FIG. 8E defines the accumulated error, and the vertical axis defines the amount of trials that resulted with that amount of errors, e.g., when the number of simulations is N=1000.

Figure 8F:
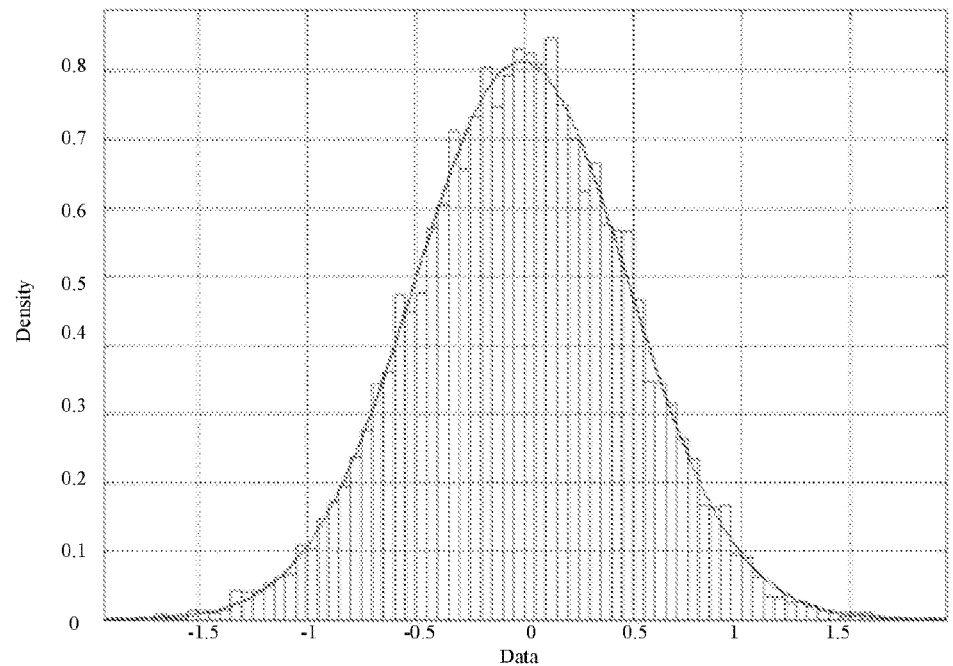

In some demonstrative embodiments, FIG. 8F depicts a histogram showing that the total error in the measured PD is within the range [−1,+1] mm for at least 95% of the cases.

Figure 9:
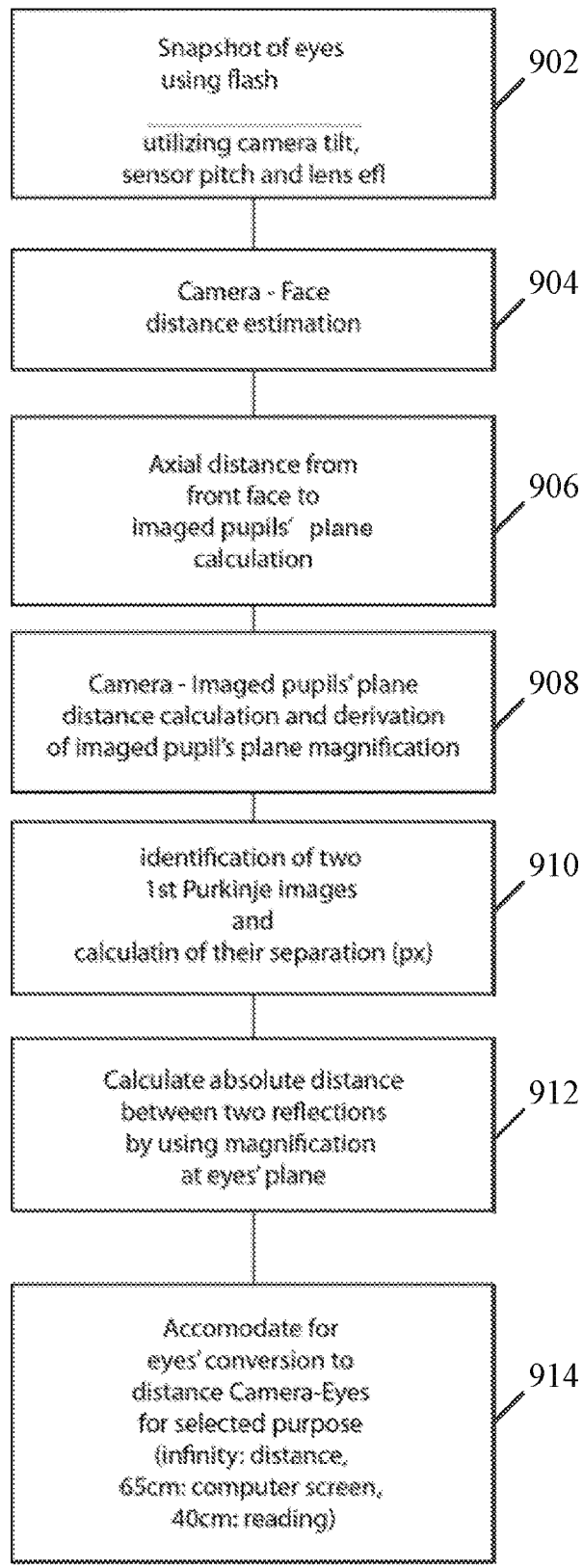
FIG. 9 is a schematic flow-chart illustration of a method of determining a pupillary distance (PD) of a user, in accordance with some demonstrative embodiments.

Reference is made to FIG. 9, which schematically illustrates a method of determining a PD of a user, in accordance with some demonstrative embodiments. For example, one or operations of the method of FIG. 9 may be performed by a mobile device, device 102 (FIG. 1), a server, e.g., server 170 (FIG. 1), and/or an application, e.g., application 160 (FIG. 1).

As indicated at block 902, the method may include capturing an image of eyes of a user looking at the flash of a camera, and receiving information relating to an orientation of the camera, the sensor pitch of the camera, and the EFL of the lens of the camera. For example, application 160 (FIG. 1) may receive the captured image including the first and second reflections from camera 118 (FIG. 1), and may receive the orientation information, the sensor pitch, and the EFL of camera 118 (FIG. 1), e.g., as described above.

As indicated at block 904, the method may include estimating a distance from the camera to an object on the face of the user. For example, application 160 (FIG. 1) may estimate the distance between camera 118 and the reference object, for example, using information from the 3D sensor 124 (FIG. 1), the acceleration information from accelerometer 128 (FIG. 1), and/or based on dimensions of the object, e.g., as described above.

As indicated at block 906, the method may include calculating an axial offset between an object plane including the object and a pupils-plane including the pupils of the user, for example, based on the camera orientation. For example, application 160 (FIG. 1) may determine the axial offset between the object plane and the pupils plane, for example, based on the orientation information from orientation estimator 128 (FIG. 1), e.g., as described above.

As indicated at block 908, the method may include determining a magnification at the pupils-plane, based on the axial distance and the measured distance from the camera to the object, for example, using the EFL and the sensor pitch. For example, application 160 (FIG. 1) may determine the magnification at the pupils-plane, for example, based on the axial offset and the distance from camera 118 (FIG. 1) to the object, e.g., as described above.

As indicated at block 910, the method may include identifying first and second reflections of the flash on the eyes of the user, and measuring the distance, e.g., in pixels, between the first reflection and the second reflection. For example, application 160 (FIG. 1) may estimate the distance, e.g., in pixels, between the first reflection and the second reflection, e.g., as described above.

As indicated at block 912, the method may include converting the distance in pixels into distance units, for example, according to the magnification at the pupils plane. For example, application 160 (FIG. 1) may estimate the distance between the first reflection and the second reflection, e.g., as described above.

As indicated at block 914, the method may include accommodating the measured distance for eye convergence, for example, by calculating where the first and second reflections would have been imaged for eyes looking to infinity, and setting the inter pupillary distance for far distance spectacles based on the accommodation. For example, application 160 (FIG. 1) may determine the pupillary distance PDinfinity, for example, based on the distance τ, e.g., as described above.

In some demonstrative embodiments, the method may optionally include calculating where the first and second reflections would have been imaged for an eye rotation to a near distance, for example, a predefined distance of 45 centimeter, and setting the near pupillary distance for near vision.

In some demonstrative embodiments, a method of determining a PD of a user may include, for example, only some of the operations of FIG. 9, for example, while not including one or more other operations of the method of FIG. 9.

In some demonstrative embodiments, a method of determining a PD may be performed, for example, even without performing one or more, e.g., all, of the operations described above with respect to blocks 906 and/or 908, for example, if a distance between the camera and the pupils is known, or determined.

In some demonstrative embodiments, the distance between the camera and the pupils may be determined, for example, based on a size of a facial future of the face of the user.

In one example, the method of determining a PD may include calibrating and/or measuring a size of the facial feature, e.g., an Iris diameter; capturing an image of the face using the flash of the camera; and determining the distance from the camera to the pupils, for example, based on the facial feature.

In some demonstrative embodiments, calibrating and/or measuring the facial feature may be, for example, by capturing in an image including the facial object and a reference object, e.g., a credit card, which may be placed on the face of the user.

For example, a user may cover one eye of the user with the reference object, e.g., the credit card, for example, to enable a calibration of a diameter of an iris of the other eye.

Figure 10:
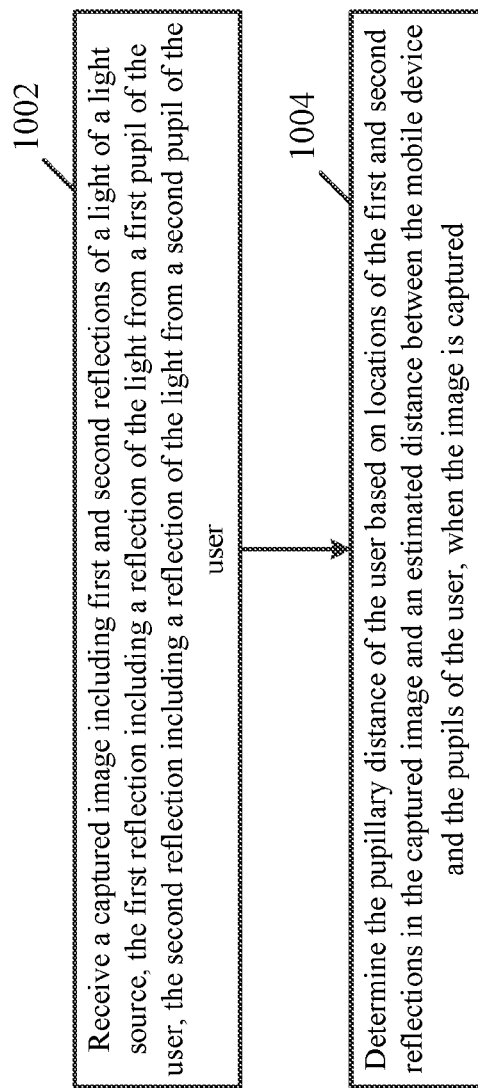
FIG. 10 is a schematic flow-chart illustration of a method of determining a PD of a user, in accordance with some demonstrative embodiments.

Reference is made to FIG. 10, which schematically illustrates a method of determining a PD of a user, in accordance with some demonstrative embodiments. For example, one or operations of the method of FIG. 10 may be performed by a mobile device, device 102 (FIG. 1), a server, e.g., server 170 (FIG. 1), and/or an application, application 160 (FIG. 1)

As indicated at block 1002, the method may include receiving a captured image including first and second reflections of light of a light source, the first reflection including a reflection of the light from a first pupil of the user. For example, application 160 (FIG. 1) may receive the captured image including the first and second reflections, e.g., as described above.

As indicated at block 1004, the method may include determining the pupillary distance based on locations of the first and second reflections in the captured image and an estimated distance between a camera used to capture the image and the pupils of the user, when the image is captured. For example, application 160 (FIG. 1) may determine the pupillary distance of the user, for example, based on locations of the first and second reflections in the captured image and an estimated distance between device 102 (FIG. 1) and the pupils of the user, when the image is captured, e.g., as described above.

Figure 11:
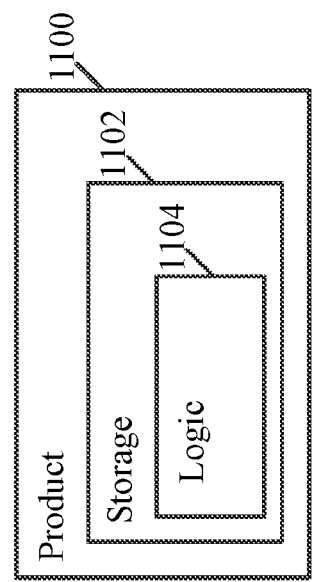
FIG. 11 is a schematic illustration of a product, in accordance with some demonstrative embodiments.

Reference is made to FIG. 11, which schematically illustrates a product of manufacture 1000, in accordance with some demonstrative embodiments. Product 1100 may include one or more tangible computer-readable non-transitory storage media 1102, which may include computer-executable instructions, e.g., implemented by logic 1104, operable to, when executed by at least one computer processor, enable the at least one computer processor to implement one or more operations at device 102 (FIG. 1), server 170 (FIG. 1), and/or application 160 (FIG. 1), and/or to perform, trigger and/or implement one or more operations, communications and/or functionalities according to FIGS. 1-10, and/or one or more operations described herein. The phrase "non-transitory machine-readable medium" is directed to include all computer-readable media, with the sole exception being a transitory propagating signal.

In some demonstrative embodiments, product 1100 and/or machine-readable storage medium 1102 may include one or more types of computer-readable storage media capable of storing data, including volatile memory, non-volatile memory, removable or non-removable memory, erasable or non-erasable memory, writeable or re-writeable memory, and the like. For example, machine-readable storage medium 1102 may include, RAM, DRAM, Double-Data-Rate DRAM (DDR-DRAM), SDRAM, static RAM (SRAM), ROM, programmable ROM (PROM), erasable programmable ROM (EPROM), electrically erasable programmable ROM (EEPROM), Compact Disk ROM (CD-ROM), Compact Disk Recordable (CD-R), Compact Disk Rewriteable (CD-RW), flash memory (e.g., NOR or NAND flash memory), content addressable memory (CAM), polymer memory, phase-change memory, ferroelectric memory, silicon-oxide-nitride-oxide-silicon (SONOS) memory, a disk, a floppy disk, a hard drive, an optical disk, a magnetic disk, a card, a magnetic card, an optical card, a tape, a cassette, and the like. The computer-readable storage media may include any suitable media involved with downloading or transferring a computer program from a remote computer to a requesting computer carried by data signals embodied in a carrier wave or other propagation medium through a communication link, e.g., a modem, radio or network connection.

In some demonstrative embodiments, logic 1104 may include instructions, data, and/or code, which, if executed by a machine, may cause the machine to perform a method, process and/or operations as described herein. The machine may include, for example, any suitable processing platform, computing platform, computing device, processing device, computing system, processing system, computer, processor, or the like, and may be implemented using any suitable combination of hardware, software, firmware, and the like.

In some demonstrative embodiments, logic 1104 may include, or may be implemented as, software, a software module, an application, a program, a subroutine, instructions, an instruction set, computing code, words, values, symbols, and the like. The instructions may include any suitable type of code, such as source code, compiled code, interpreted code, executable code, static code, dynamic code, and the like. The instructions may be implemented according to a predefined computer language, manner or syntax, for instructing a processor to perform a certain function. The instructions may be implemented using any suitable high-level, low-level, object-oriented, visual, compiled and/or interpreted programming language, such as C, C++, Java, BASIC, Matlab, Pascal, Visual BASIC, assembly language, machine code, and the like.

Examples

The following examples pertain to further embodiments.

Example 1 includes a product comprising one or more tangible computer-readable non-transitory storage media comprising computer-executable instructions operable to, when executed by at least one computer processor, enable the at least one computer processor to implement operations of measuring a pupillary distance between pupils of a user, the operations comprising receiving a captured image comprising first and second reflections of a light of a light source, the first reflection comprising a reflection of the light from a first pupil of the user, and the second reflection comprising a reflection of the light from a second pupil of the user; and determining the pupillary distance based on locations of the first and second reflections in the captured image and an estimated distance between an image capturing device and pupils of the user, when the image is captured.

Example 2 includes the subject matter of Example 1, and optionally, wherein the captured image comprises an object on a face of the user, the estimated distance is based on one or more dimensions of the object.

Example 3 includes the subject matter of Example 2, and optionally, wherein the operations comprise determining an axial offset between the object and the pupils along an axis perpendicular to a plane including the object, and determining the pupillary distance based on the axial offset.

Example 4 includes the subject matter of Example 2 or 3, and optionally, wherein the estimated distance is based on a three dimensional (3D) Cartesian coordinate of a feature of the face.

Example 5 includes the subject matter of any one of Examples 1-4, and optionally, wherein the estimated distance is based on acceleration information indicating an acceleration of the image capturing device.

Example 6 includes the subject matter of any one of Examples 1-5, and optionally, wherein the operations comprise determining the pupillary distance based on a number of pixels between the first and second reflections, and a pixel to millimeter (mm) ratio of the pixels.

Example 7 includes the subject matter of any one of Examples 1-6, and optionally, wherein the operations comprise receiving orientation information indicating an orientation of the image capturing device when the image is captured, and determining the pupillary distance based on the orientation information.

Example 8 includes the subject matter of Example 7, and optionally, wherein the orientation information indicates a tilt angle of the image capturing device.

Example 9 includes the subject matter of any one of Examples 1-8, and optionally, wherein the operations comprise determining the pupillary distance based on one or more attributes of the image capturing device.

Example 10 includes the subject matter of Example 9, and optionally, wherein the one or more attributes comprise at least one attribute selected from the group consisting of an Effective Focal Length (EFL) of a lens of the image capturing device, a horizontal field of view of a sensor of the image capturing device, a vertical field of view of the sensor, a resolution of the sensor, and a distance between two adjacent pixels of the sensor.

Example 11 includes the subject matter of any one of Examples 1-10, and optionally, wherein the operations comprise determining the pupillary distance based on an eye radius parameter and a distance between the image capturing device and a plane comprising the pupils.

Example 12 includes the subject matter of any one of Examples 1-11, and optionally, wherein the pupillary distance comprises a near pupillary distance or a far pupillary distance.

Example 13 includes a mobile device configured to measure a pupillary distance between pupils of a user, the mobile device comprising a camera to capture an image comprising first and second reflections of a light of a light source, the first reflection comprising a reflection of the light from a first pupil of the user, and the second reflection comprising a reflection of the light from a second pupil of the user; and a pupillary distance calculator to receive the captured image, and to determine the pupillary distance based on locations of the first and second reelections in the captured image and an estimated distance between the mobile device and the pupils, when the image is captured.

Example 14 includes the subject matter of Example 13, and optionally, wherein the captured image comprises an object on a face of the user, the estimated distance is based on one or more dimensions of the object.

Example 15 includes the subject matter of Example 14, and optionally, wherein the mobile device is configured to determine an axial offset between the object and the pupils along an axis perpendicular to a plane including the object, and to determine the pupillary distance based on the axial offset.

Example 16 includes the subject matter of Example 14 or 15, and optionally, wherein the estimated distance is based on a three dimensional (3D) Cartesian coordinate of a feature of the face.

Example 17 includes the subject matter of any one of Examples 13-16, and optionally, wherein the estimated distance is based on acceleration information indicating an acceleration of the image capturing device.

Example 18 includes the subject matter of any one of Examples 13-17, and optionally, wherein the mobile device is configured to determine the pupillary distance based on a number of pixels between the first and second reflections, and a pixel to millimeter (mm) ratio of the pixels.

Example 19 includes the subject matter of any one of Examples 13-18, and optionally, wherein the mobile device is configured to receive orientation information indicating an orientation of the image capturing device when the image is captured, and to determine the pupillary distance based on the orientation information.

Example 20 includes the subject matter of Example 19, and optionally, wherein the orientation information indicates a tilt angle of the image capturing device.

Example 21 includes the subject matter of any one of Examples 13-20, and optionally, wherein the mobile device is configured to determine the pupillary distance based on one or more attributes of the image capturing device.

Example 22 includes the subject matter of Example 21, and optionally, wherein the one or more attributes comprise at least one attribute selected from the group consisting of an Effective Focal Length (EFL) of a lens of the image capturing device, a horizontal field of view of a sensor of the image capturing device, a vertical field of view of the sensor, a resolution of the sensor, and a distance between two adjacent pixels of the sensor.

Example 23 includes the subject matter of any one of Examples 13-22, and optionally, wherein the operations comprise determining the pupillary distance based on an eye radius parameter and a distance between the image capturing device and a plane comprising the pupils.

Example 24 includes the subject matter of any one of Examples 13-23, and optionally, wherein the pupillary distance comprises a near pupillary distance or a far pupillary distance.

Example 25 includes a method of measuring a pupillary distance between pupils of a user, the method comprising receiving a captured image comprising first and second reflections of a light of a light source, the first reflection comprising a reflection of the light from a first pupil of the user, and the second reflection comprising a reflection of the light from a second pupil of the user; and determining the pupillary distance based on locations of the first and second reflections in the captured image and an estimated distance between an image capturing device and pupils of the user, when the image is captured.

Example 26 includes the subject matter of Example 25, and optionally, wherein the captured image comprises an object on a face of the user, the estimated distance is based on one or more dimensions of the object.

Example 27 includes the subject matter of Example 26, and optionally, comprising determining an axial offset between the object and the pupils along an axis perpendicular to a plane including the object, and determining the pupillary distance based on the axial offset.

Example 28 includes the subject matter of Example 26 or 27, and optionally, wherein the estimated distance is based on a three dimensional (3D) Cartesian coordinate of a feature of the face.

Example 29 includes the subject matter of any one of Examples 25-28, and optionally, wherein the estimated distance is based on acceleration information indicating an acceleration of the image capturing device.

Example 30 includes the subject matter of any one of Examples 25-29, and optionally, comprising determining the pupillary distance based on a number of pixels between the first and second reflections, and a pixel to millimeter (mm) ratio of the pixels.

Example 31 includes the subject matter of any one of Examples 25-30, and optionally, comprising receiving orientation information indicating an orientation of the image capturing device when the image is captured, and determining the pupillary distance based on the orientation information.

Example 32 includes the subject matter of Example 31, and optionally, wherein the orientation information indicates a tilt angle of the image capturing device.

Example 33 includes the subject matter of any one of Examples 25-32, and optionally, comprising determining the pupillary distance based on one or more attributes of the image capturing device.

Example 34 includes the subject matter of Example 33, and optionally, wherein the one or more attributes comprise at least one attribute selected from the group consisting of an Effective Focal Length (EFL) of a lens of the image capturing device, a horizontal field of view of a sensor of the image capturing device, a vertical field of view of the sensor, a resolution of the sensor, and a distance between two adjacent pixels of the sensor.

Example 35 includes the subject matter of any one of Examples 25-34, and optionally, comprising determining the pupillary distance based on an eye radius parameter and a distance between the image capturing device and a plane comprising the pupils.

Example 36 includes the subject matter of any one of Examples 25-35, and optionally, wherein the pupillary distance comprises a near pupillary distance or a far pupillary distance.

Example 37 includes an apparatus to measure a pupillary distance between pupils of a user, the apparatus comprising means for receiving a captured image comprising first and second reflections of a light of a light source, the first reflection comprising a reflection of the light from a first pupil of the user, and the second reflection comprising a reflection of the light from a second pupil of the user; and means for determining the pupillary distance based on locations of the first and second reflections in the captured image and an estimated distance between an image capturing device and pupils of the user, when the image is captured.

Example 38 includes the subject matter of Example 37, and optionally, wherein the captured image comprises an object on a face of the user, the estimated distance is based on one or more dimensions of the object.

Example 39 includes the subject matter of Example 38, and optionally, comprising means for determining an axial offset between the object and the pupils along an axis perpendicular to a plane including the object, and determining the pupillary distance based on the axial offset.

Example 40 includes the subject matter of Example 38 or 39, and optionally, wherein the estimated distance is based on a three dimensional (3D) Cartesian coordinate of a feature of the face.

Example 41 includes the subject matter of any one of Examples 37-40, and optionally, wherein the estimated distance is based on acceleration information indicating an acceleration of the image capturing device.

Example 42 includes the subject matter of any one of Examples 37-41, and optionally, comprising means for determining the pupillary distance based on a number of pixels between the first and second reflections, and a pixel to millimeter (mm) ratio of the pixels.

Example 43 includes the subject matter of any one of Examples 37-42, and optionally, comprising means for receiving orientation information indicating an orientation of the image capturing device when the image is captured, and determining the pupillary distance based on the orientation information.

Example 44 includes the subject matter of Example 43, and optionally, wherein the orientation information indicates a tilt angle of the image capturing device.

Example 45 includes the subject matter of any one of Examples 37-44, and optionally, comprising means for determining the pupillary distance based on one or more attributes of the image capturing device.

Example 46 includes the subject matter of Example 45, and optionally, wherein the one or more attributes comprise at least one attribute selected from the group consisting of an Effective Focal Length (EFL) of a lens of the image capturing device, a horizontal field of view of a sensor of the image capturing device, a vertical field of view of the sensor, a resolution of the sensor, and a distance between two adjacent pixels of the sensor.

Example 47 includes the subject matter of any one of Examples 37-46, and optionally, comprising means for determining the pupillary distance based on an eye radius parameter and a distance between the image capturing device and a plane comprising the pupils.

Example 48 includes the subject matter of any one of Examples 37-47, and optionally, wherein the pupillary distance comprises a near pupillary distance or a far pupillary distance.

Functions, operations, components and/or features described herein with reference to one or more embodiments, may be combined with, or may be utilized in combination with, one or more other functions, operations, components and/or features described herein with reference to one or more other embodiments, or vice versa.

While certain features have been illustrated and described herein, many modifications, substitutions, changes, and equivalents may occur to those skilled in the art. It is, therefore, to be understood that the appended claims are intended to cover all such modifications and changes as fall within the true spirit of the disclosure.

What is claimed is:

1. A product comprising one or more tangible computer-readable non-transitory storage media comprising computer-executable instructions operable to, when executed by at least one computer processor, enable the at least one computer processor to implement operations of measuring a pupillary distance between pupils of a user, the instructions, when executed, result in:

processing image information captured by a sensor of a user device;

based on the image information, identifying locations of first and second reflections of a light of a light source of the user device, the first reflection comprising a reflection of said light from a pupil of a first eye of said user, and the second reflection comprising a reflection of said light from a pupil of a second eye of said user, wherein identifying the locations of the first and second reflections comprises identifying the location of the first reflection by identifying a first Purkinje image of a reflection of the light of the light source by an outer reflecting cornea surface of the first eye, and identifying the location of the second reflection by identifying a first Purkinje image of a reflection of the light of the light source by an outer reflecting cornea surface of the second eye;

determining a first estimated distance, the first estimated distance is between the sensor and the pupils of the user when the image information is captured by the sensor;

determining, a second estimated distance between the locations of the first and second reflections based on a distance between the first Purkinje image of the reflection of the light of the light source by the outer reflecting cornea surface of the first eye, and the first Purkinje image of the reflection of the light of the light source by the outer reflecting cornea surface of the second eye; and determining the pupillary distance based on the first estimated distance and the second estimated distance.

2. The product of claim 1, wherein said image information comprises information of an object or feature on a face of said user, wherein the instructions, when executed, result in determining said first estimated distance based on one or more dimensions of said object or feature.

3. The product of claim 2, wherein the instructions, when executed, result in determining an axial offset between said object or feature and said pupils along an axis perpendicular to a plane including said object or feature, and determining the pupillary distance based on said axial offset.

4. The product of claim 1, wherein said instructions, when executed, result in determining said first estimated distance based on a three dimensional (3D) Cartesian coordinate of a feature of said face.

5. The product of claim 1, wherein said instructions, when executed, result in determining said first estimated distance based on acceleration information indicating an acceleration of said user device.

6. The product of claim 1, wherein said instructions, when executed, result in determining the pupillary distance based on a number of pixels between the locations of said first and second reflections, and a pixel to millimeter (mm) ratio of said pixels.

7. The product of claim 1, wherein said instructions, when executed, result in receiving orientation information indicating an orientation of said user device when said image information is captured, and determining the pupillary distance based on said orientation information.

8. The product of claim 7, wherein said orientation information indicates a tilt angle of said user device.

9. The product of claim 1, wherein the instructions, when executed, result in determining the pupillary distance based on one or more attributes of the sensor.

10. The product of claim 9, wherein said one or more attributes comprise at least one attribute selected from the group consisting of an Effective Focal Length (EFL) of a lens of said sensor, a horizontal field of view of said sensor, a vertical field of view of said sensor, a resolution of said sensor, and a distance between two adjacent pixels of said sensor.

11. The product of claim 1, wherein the instructions, when executed, result in determining the pupillary distance based on an eye radius parameter and a distance between the sensor and a plane comprising said pupils.

12. The product of claim 1, wherein the pupillary distance comprises a near pupillary distance or a far pupillary distance.

13. The product of claim 1, wherein the instructions, when executed, result in triggering the light source of the user device to generate the light to illuminate the pupils when the sensor is to capture the image information.

14. A mobile device configured to measure a pupillary distance between pupils of a user, the mobile device comprising:

a light source to generate light to illuminate the pupils of the user;

a sensor to capture image information corresponding to the pupils of the user; and a processor configured to identify, based on the image information, locations of first and second reflections of the light of the light source of the mobile device, the first reflection comprising a reflection of said light from a pupil of a first eye of said user, and the second reflection comprising a reflection of said light from a pupil of a second eye of said user, the processor configured to identify the location of the first reflection by identifying a first Purkinje image of a reflection of the light of the light source by an outer reflecting cornea surface of the first eye, and to identify the location of the second reflection by identifying a first Purkinje image of a reflection of the light of the light source by an outer reflecting cornea surface of the second eye, the processor configured to determine a first estimated distance, the first estimated distance is between the sensor and the pupils of the user when the image information is captured by the sensor, to determine a second estimated distance between the locations of the first and second reflections based on a distance between the first Purkinje image of the reflection of the light of the light source by the outer reflecting cornea surface of the first eye, and the first Purkinje image of the reflection of the light of the light source by the outer reflecting cornea surface of the second eye, and to determine the pupillary distance based on the first estimated distance and the second estimated distance.

15. The mobile device of claim 14, wherein said image information comprises information of an object or feature on a face of said user, said processor configured to determine the first estimated distance based on one or more dimensions of said object or feature.

16. The mobile device of claim 14, wherein the processor is configured to determine the pupillary distance based on a number of pixels between the locations of said first and second reflections, and a pixel to millimeter (mm) ratio of said pixels.

17. The mobile device of claim 14, wherein the processor is configured to receive orientation information indicating an orientation of said mobile device when said image information is captured, and to determine the pupillary distance based on said orientation information.

18. The mobile device of claim 14, wherein the light source comprises a Light Emitting Diode (LED).

19. The mobile device of claim 14, wherein the processor is configured to determine the pupillary distance based on an eye radius parameter and a distance between the sensor and a plane comprising said pupils.

20. A method of measuring a pupillary distance between pupils of a user, the method comprising:

processing image information captured by a sensor of a user device;

based on the image information, identifying locations of first and second reflections of a light of a light source of the user device, the first reflection comprising a reflection of said light from a pupil of a first eye of said user, and the second reflection comprising a reflection of said light from a pupil of a second eye of said user, wherein identifying the locations of the first and second reflections comprises identifying the location of the first reflection by identifying a first Purkinje image of a reflection of the light of the light source by an outer reflecting cornea surface of the first eye, and identifying the location of the second reflection by identifying a first Purkinje image of a reflection of the light of the light source by an outer reflecting cornea surface of the second eye;

determining a first estimated distance, the first estimated distance is between the sensor and the pupils of the user when the image information is captured by the sensor;

determining a second estimated distance between the locations of the first and second reflections based on a distance between the first Purkinje image of the reflection of the light of the light source by the outer reflecting cornea surface of the first eye, and the first Purkinje image of the reflection of the light of the light source by the outer reflecting cornea surface of the second eye; and determining the pupillary distance based on the first estimated distance and the second estimated distance.

21. The method of claim 20, wherein said image information comprises information of an object or feature on a face of said user, and determining said first estimated distance is based on one or more dimensions of said object or feature.

22. The method of claim 20 comprising determining the pupillary distance based on a number of pixels between the locations of said first and second reflections, and a pixel to millimeter (mm) ratio of said pixels.

23. The method of claim 20 comprising determining the pupillary distance based on one or more attributes of the sensor.

24. The method of claim 20 comprising determining the pupillary distance based on an eye radius parameter and a distance between the sensor and a plane comprising said pupils.

\* \* \* \* \*